(12) United States Patent
Oohashi et al.

(10) Patent No.: US 7,079,659 B1
(45) Date of Patent: Jul. 18, 2006

(54) SOUND GENERATING APPARATUS AND METHOD, SOUND GENERATING SPACE AND SOUND, EACH PROVIDED FOR SIGNIFICANTLY INCREASING CEREBRAL BLOOD FLOWS OF PERSONS

(75) Inventors: Tsutomu Oohashi, Tokyo (JP); Norie Kawai, Tsukuba (JP); Emi Nishina, Tokyo (JP); Yoshitaka Fuwamotot, Chiba (JP); Reiko Yagi, Chigasaki (JP); Masako Morimoto, Tokyo (JP)

(73) Assignee: Advanced Telecommunications Research Institute International, Kyoto (JP)

(*) Notice: Subject to any disclaimer, the term of this patent is extended or adjusted under 35 U.S.C. 154(b) by 0 days.

(21) Appl. No.: 08/723,955

(22) Filed: Sep. 26, 1996

(30) Foreign Application Priority Data

Mar. 26, 1996 (JP) .................... P8-069923

(51) Int. Cl.
*A61M 21/00* (2006.01)
(52) U.S. Cl. .................. 381/98; 600/27; 600/28
(58) Field of Classification Search ............. 381/98, 381/103; 600/26, 27, 28; 601/1, 2; 128/897, 128/898
See application file for complete search history.

(56) References Cited

U.S. PATENT DOCUMENTS 3,835,833 A * 9/1974 Limoge ................. 600/26
5,581,626 A * 12/1996 Palmer ................. 381/103
5,638,826 A * 6/1997 Wolpaw et al. ............ 600/544
5,734,730 A * 3/1998 Cho et al. ................ 381/98
5,954,630 A * 9/1999 Masaki et al.

FOREIGN PATENT DOCUMENTS

| JP | 0218463 | 8/1989 |
| JP | 2279163 | 11/1990 |
| JP | 3-210274 | 9/1991 |
| JP | 7-22749 | 4/1995 |

OTHER PUBLICATIONS

Tsutomu Oohashi et al., "High Frequency Sound Above the Audible Range Affects Brain Electric Activity and Sound Perception", the 91st Conventional of AES, an Audio Engineering Society, 3207(W-1), 8M(W1), New York, Oct. 1991.
T. Oohashi et al., "Activation of Deep Brain Structures by Sounds Frequencies Above the Audible Range in Human", Fourth IBRO World Congress of Neuroscience, Kyoto, Japan, Jul. 1995.

(Continued)

*Primary Examiner*—Brian T. Pendleton
(74) *Attorney, Agent, or Firm*—Birch, Stewart, Kolasch & Birch, LLP

(57) ABSTRACT

In a sound generating apparatus, a sound generating space, a sound, and a method for generating a sound, a sound is generated which has a frequency within a first frequency range beyond a predetermined audible frequency range and up to a predetermined maximum frequency, and which is non-stationary so as to change in a micro-temporal area in a second frequency range beyond 10 kHz. Then, the generated sound is applied to a person, thereby increasing cerebral blood flows of the person. This causes improvement and enhancement of the person's state of mind and body, so as to relieve stresses, thereby relaxing the person.

20 Claims, 27 Drawing Sheets

First Preferred Embodiment

OTHER PUBLICATIONS

T. Oohashi et al., "Amenity Sound Assessment by Power Spectrum and Fluctuation Structure"; Proceeding of 9th Symposium on Human Interface, No. 2412, pp. 545-552, Kobe, Japan, Oct. 18-20, 1993.

T. Oohashi et al., "Information Science on Amenity Sound Environment"; Bulletin of National Institute of Multimedia Education, No. 7, pp. 53-101, Chiba, Japan, 1992.

Yoshitaka Fuwamoto et al., "On the Fluctuation Structure in the Micro-temporal Area in the Sounds Produced by Musical Instruments of Two kind of Cultures"; National Institute of Multimedia Education, University of Tokyo, pp. 639-640, Sep. 27, 1995.

* cited by examiner

Fig. 1  First Preferred Embodiment

Second Preferred Embodiment

Parts 100 and 200 in which Cerebral Blood Flows Significantly increase in Full Range Sound as compared with that in High Cut Sound Sagittal Projection Coronal Projection Transversal Projection Part 100 in which Cerebral Blood Flow Significantly increases in Full Range Sound as compared with that in High Cut Sound
Talairach Coordinates (x=4mm, y=−26mm, z=−8mm)
Z Score=4.67
Brainstem Sagittal Cross Section Coronal Cross Section Transversal Cross Section Part 200 in which Cerebral Blood Flow Significantly increases in Full Range Sound as compared with that in High Cut Sound
Talairach Coordinates (x=−16mm, y=−18mm, z=0mm)
Z Score=4.50
Left Thalamus Sagittal Cross Section Coronal Cross Section Transversal Cross Section 300 : Part in which α-EEG Potential significantly correlates with r-CBF Value 101 : Part in which Cerebral Blood Flow significantly increase Parts 400, 401 and 402
in which r-CBF Values significantly increase in
the case of High Cut Sound from Earphone and Low
Cut Sound from Speaker as compared with only High
Cut Sound from Earphone Sagittal Projection Coronal Projection Transversal Projection Talairach Coordinates
(x,y,z)=(28mm,-54mm,28mm): Angular Gyrus of Right Brain Sagittal Cross Section Coronal Cross Section Transversal Cross Section Talairach Coordinates (x, y, z) = (14mm, -34mm, 32mm): Posterior Cingulate Gyrus Sagittal Cross Section Coronal Cross Section Transversal Cross Section Talairach Coordinates (x,y,z)=(10mm,-30mm,44mm): Precuneus Sagittal Cross Section Coronal Cross Section Transversal Cross Section

SOUND GENERATING APPARATUS AND METHOD, SOUND GENERATING SPACE AND SOUND, EACH PROVIDED FOR SIGNIFICANTLY INCREASING CEREBRAL BLOOD FLOWS OF PERSONS

BACKGROUND OF THE INVENTION

1. Field of the Invention

The present invention relates to a sound generating apparatus, a sound generating space, a sound, and a method for generating a sound, and in particular, a sound generating apparatus, a sound generating space, a sound, a method for generating a sound, each provided for significantly increasing cerebral blood flows of a person.

2. Description of the Prior Art

It is generally accepted that audio frequencies above 20 kHz do not affect human sensory perception since they are beyond the audible range. Due to this, the sampling frequency for compact discs (CDs) and mini discs (MDs) is set to 44.1 kHz, and the equipments for these discs are manufactured so that audio signals up to about 22 kHz can be recorded and reproduced. Also, the sampling frequency for digital audio tape recorders (DATs) as well as digital compact cassette recorders (DCCs) can be set to any one of the frequencies, 48 kHz, 44.1 kHz, and 32 kHz, and the equipments for these are manufactured so that audio signals up to about 24 kHz can be recorded and reproduced. Thus, generally, human being is allowed to relax himself or herself by listening to favorite music with the use of these equipments.

On the other hand, the strength of $\alpha$-EEG ($\alpha$-electroencephalogram) or $\alpha$ wave generated from the human brain is generally used as an index indicating that one has less stress. Taking advantage of the fact that when a ultra-low frequency signal of around 10 Hz is generated and heard or listened to, one will generate $\alpha$-EEG, there have been developed and marketed apparatuses for generating such an ultra-low frequency signal.

However, in the above-mentioned prior art, there are such problems that, the degree to which stresses can be relieved would change depending on the contents of the music or the frequencies of the ultra-low frequency signal, and moreover the degree thereto would be relatively small.

SUMMARY OF THE INVENTION

An essential object of the present invention is therefore to provide a sound generating apparatus capable of increasing cerebral blood flows of a person so as to improve and enhance his or her state of mind and body, to relieve stresses, thereby relaxing him or her.

Another object of the present invention is to provide a sound generating space capable of increasing cerebral blood flows of a person so as to improve and enhance his or her state of mind and body, to relieve stresses, thereby relaxing him or her.

A further object of the present invention is to provide a sound capable of increasing cerebral blood flows of a person so as to improve and enhance his or her state of mind and body, to relieve stresses, thereby relaxing him or her.

A still further object of the present invention is to provide a method for generating a sound, capable of increasing cerebral blood flows of a person so as to improve and enhance his or her state of mind and body, to relieve stresses, thereby relaxing him or her.

In order to achieve the aforementioned objective, according to one aspect of the present invention, there is provided a sound generating apparatus that generates a sound which has a frequency within a first frequency range beyond a predetermined audible frequency range and up to a predetermined maximum frequency, and which is non-stationary so as to change in a micro-temporal area in a second frequency beyond 10 kHz; and that applies the sound to a person, thereby increasing cerebral blood flows of the person.

According to another aspect of the present invention, there is provided a sound generating apparatus that generates a sound which has a frequency within a first frequency range beyond a predetermined audible frequency range and up to a predetermined maximum frequency, and which is non-stationary so as to change in a micro-temporal area in a second frequency range beyond 10 kHz;

that applies first sound components within the audible frequency range out of said sound to an auditory sensation of a person; and that applies second sound components having a frequency range beyond the audible frequency range out of said sound to the person, thereby increasing cerebral blood flows of the person.

In the above-mentioned sound generating apparatus, the maximum frequency is preferably 150 kHz.

According to a further aspect of the present invention, there is provided a sound generating space that generates a sound which has a frequency within a first frequency range beyond a predetermined audible frequency range and up to a predetermined maximum frequency, and which is non-stationary so as to change in a micro-temporal area in a second frequency range beyond 10 kHz; and that applies said sound to a person, thereby increasing cerebral blood flows of the person.

According to a still further aspect of the present invention, there is provided a sound generating space that generates a sound which has a frequency within a first frequency range beyond a predetermined audible frequency range and up to a predetermined maximum frequency, and which is non-stationary so as to change in a micro-temporal area in a second frequency range beyond 10 kHz;

that applies first sound components within the audible frequency range out of said sound are applied to an auditory sensation of a person; and that applies second sound components having a frequency range beyond the audible frequency range out of said sound are applied to the person, thereby increasing cerebral blood flows of the person.

In the above-mentioned sound generating space, the maximum frequency is preferably 150 kHz.

According to a still more further aspect of the present invention, there is provided a sound which has a frequency within a first frequency range beyond a predetermined audible frequency range and up to a predetermined maximum frequency, and which is non-stationary so as to change in a micro-temporal area in a second frequency range beyond 10 kHz, said sound being applied to a person, thereby increasing cerebral blood flows of the person.

In the above-mentioned sound, the maximum frequency is preferably 150 kHz.

According to a more still further aspect of the present invention, there is provided a method for generating a sound, including the following steps of:

generating a sound which has a frequency within a first frequency range beyond a predetermined audible frequency range and up to a predetermined maximum frequency, and which is non-stationary so as to change in a micro-temporal area in a second frequency range beyond 10 kHz; and applying said sound to a person, thereby increasing cerebral blood flows of the person.

According to a more still more further aspect of the present invention, there is provided a method for generating a sound, including the following steps of:

generating a sound which has a frequency within a first frequency range beyond a predetermined audible frequency range and up to a predetermined maximum frequency, and which is non-stationary so as to change in a micro-temporal area in a second frequency range beyond 10 kHz;

applying first sound components within the audible frequency range out of said sound to an auditory sensation of a person; and applying second sound components having a frequency range beyond the audible frequency range out of said sound to the person, thereby increasing cerebral blood flows of the person.

According to the present invention, therefore, when applying the sound to the person as described above, the α-EEG potential can be increased so that the person can be relaxed, with stresses dissipated, and that the comfortability of the mind as well as the health of the body can be enhanced or maintained successful.

BRIEF DESCRIPTION OF THE DRAWINGS

These and other objects and features of the present invention will become clear from the following description taken in conjunction with the preferred embodiments thereof with reference to the accompanying drawings throughout which like parts are designated by like reference numerals, and in which:

FIG. 9A is a sagittal projection which is a projection along the sagittal suture of the human skull, FIG. 9B is a coronal projection which is a projection along the coronal suture of the skull, and FIG. 9C is a transversal projection of the skull;

FIG. 10A is a longitudinal sectional view showing a sagittal cross section along the sagittal suture of the human skull, FIG. 10B is a longitudinal sectional view showing coronal cross section along the coronal suture of the skull, and FIG. 10C is a transversal cross sectional view of the skull;

FIG. 11A is a longitudinal sectional view showing a sagittal cross section along the sagittal suture of the human skull, FIG. 11B is a longitudinal sectional view showing a coronal cross section along the coronal suture of the skull, and FIG. 11C is a transversal cross sectional view of the skull;

FIG. 12A is a graph showing the r-CBF values at the brainstem, and FIG. 12B is a graph showing the r-CBF values at the left thalamus;

FIG. 14A is a graph showing the r-CBF values at the brainstem, and FIG. 14B is a graph showing the r-CBF values at the left thalamus;

FIG. 16A shows the cross section for z=−4 mm, FIG. 16B shows the cross section for z=0 mm, and FIG. 16C shows the cross section for z=4 mm;

FIG. 19A is a sagittal projection which is a projection along the sagittal suture of the human skull, FIG. 19B is a coronal projection which is a projection along the coronal suture of the skull, and FIG. 19C is a transversal projection of the skull;

FIG. 23A is a longitudinal sectional view showing a sagittal cross section along the sagittal suture of the human skull, FIG. 23B is a longitudinal sectional view showing a coronal cross section along the coronal suture of the skull, and FIG. 23C is a transversal cross sectional view of the skull;

FIG. 24A is a longitudinal sectional view showing a sagittal cross section along the sagittal suture of the human skull, FIG. 24B is a longitudinal sectional view showing a coronal cross section along the coronal suture of the skull, and FIG. 24C is a transversal cross sectional view of the skull;

FIG. 25A is a longitudinal sectional view showing a sagittal cross section along the sagittal suture of the human skull, FIG. 25B is a longitudinal sectional view showing a coronal cross section along the coronal suture of the skull, and FIG. 25C is a transversal cross sectional view of the skull;

FIG. 26A is a graph showing a frequency characteristic of a frequency component outputted from a D/A converter shown in FIG. 1, FIG. 26B is a graph showing frequency characteristics of respective frequency components outputted from the speakers shown in FIG. 1, and FIG. 26C is a graph showing a frequency characteristic of the background noise in the room shown in FIG. 1.

DETAILED DESCRIPTION OF THE PREFERRED EMBODIMENTS

Preferred embodiments according to the present invention will be described below with reference to the attached drawings.

First Preferred Embodiment

Figure 1:
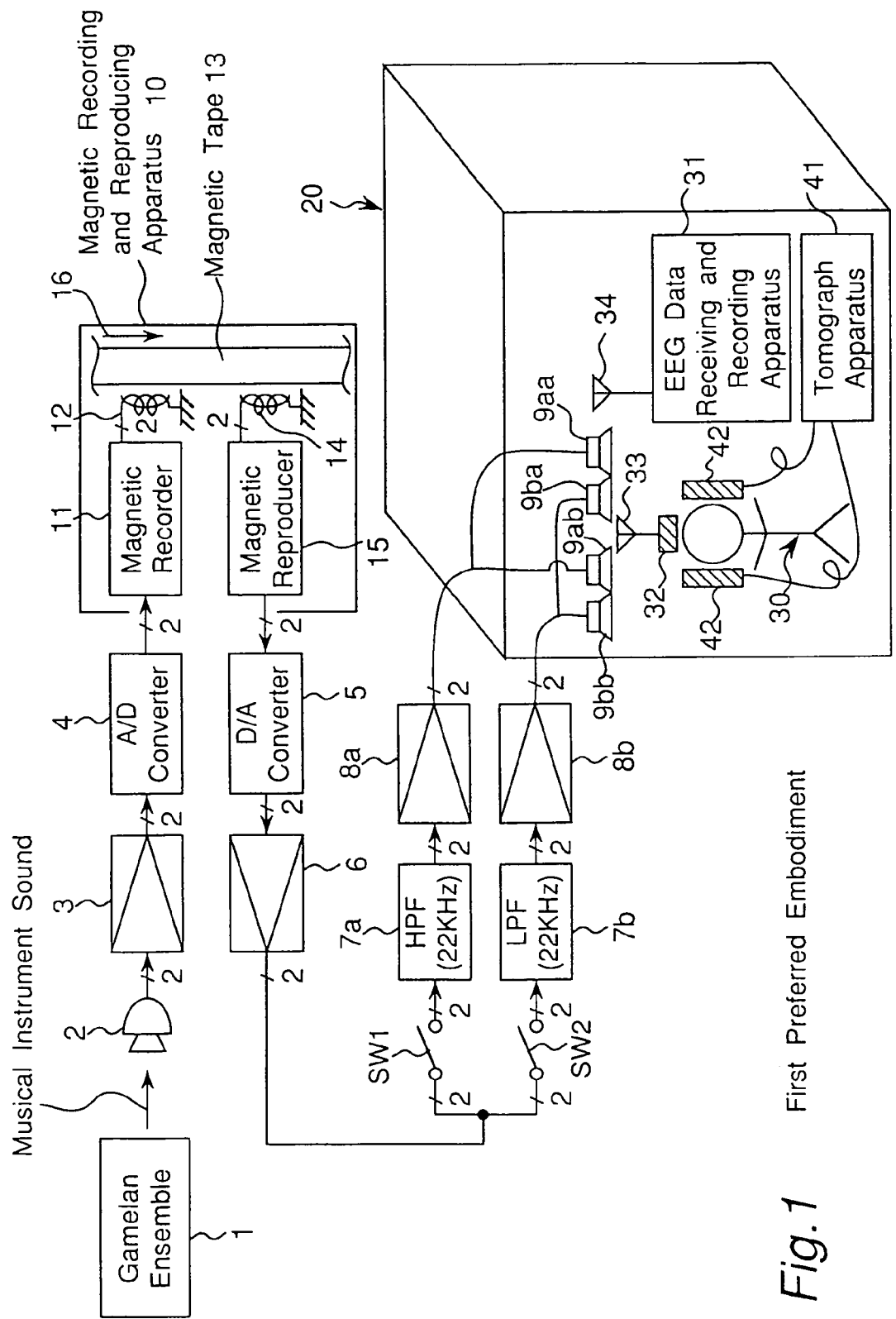
FIG. 1 is a block diagram of a signal sound generating apparatus of a first preferred embodiment according to the present invention, and a perspective view showing a room for generating signals by the signal sound generating apparatus.

FIG. 1 is a block diagram of a signal sound generating apparatus of a first preferred embodiment according to the present invention, and a perspective view showing a room 20 which is a signal sound generating space for generating signals by the signal sound generating apparatus. The signal sound generating apparatus of the present preferred embodiment is characterized in generating a signal which has a frequency within a first frequency range beyond the audible frequency range and up to a maximum frequency, and which is non-stationary so as to change in a micro-temporal area in a second frequency range beyond 10 kHz, and then applying the above generated signal to a person, thereby increasing cerebral blood flows of the person.

It is noted that the first frequency range is a range from about 20 Hz to about 150 kHz. In the first preferred embodiment, as shown in FIG. 1, the same two line systems of the sound recording and reproducing systems are prepared and driven in the so-called stereophonic state.

As shown in FIG. 1, instrumental sounds obtained by playing the Gamelan ensemble 1, which is bronze percussion ensemble of Bali Island, Indonesia, are collected by a microphone 2. The microphone 2 converts an input instrumental sound into an analog electric signal, and the converted analog electric signal is delivered to an A/D converter 4 via a preamplifier 3. The A/D converter 4 converts the input analog electric signal into a digital signal with a sampling frequency of, for example, 1920 kHz, and then delivers the analog-to-digital converted signal to a magnetic recorder 11.

A magnetic recording and reproducing apparatus 10 is a so-called digital signal recorder which comprises the magnetic recorder 11, a recording magnetic head 12, a reproducing magnetic head 14, and a magnetic reproducer 15, and which works to record digital signals to the magnetic tape 13 or to reproduce and put out digital signals recorded on the magnetic tape 13. The magnetic recording and reproducing apparatus 10 here used is a prior art DAT (Digital Audio Tape recorder) invented by Dr. Yoshio YAMASAKI, having a uniform frequency characteristic over a frequency range up to 200 kHz. The magnetic recorder 11 modulates the carrier signal according to the digital signal inputted from the A/D converter 4 by a predetermined digital modulation method, and records the modulated signal onto the magnetic tape 13 which is running along a predetermined direction 16 indicated by an arrow of FIG. 1, by using the recording magnetic head 12. On the other hand, the magnetic reproducer 15 reproduces the modulated signal recorded on the magnetic tape 13 by using the reproducing magnetic head 14, and demodulates the reproduced modulated signal by a digital demodulation method reverse to the above-mentioned digital modulation method, so as to extract and output the digital signal from the reproduced modulated signal.

The demodulated digital signal is converted from analog to digital form into the original analog signal by a D/A converter 5, and then put out via a reproduction amplifier 6. The analog signal outputted from the reproduction amplifier 6 is inputted via a switch SW1, a high-pass filter 7a having a cut-off frequency of 22 kHz, and a power amplifier 8a, into a right speaker 9aa and a left speaker 9ab, both of which can generate signals within a frequency range from 20 kHz to 150 kHz. Moreover, the analog signal outputted from the reproduction amplifier 6 is inputted via a switch SW2, a low-pass filter 7b having a cut-off frequency of 22 kHz, and a power amplifier 8b, into a right speaker 9ba and a left speaker 9bb, both of which can generate signals below 30 kHz. In the present preferred embodiment, accordingly, the crossover frequency of the two filters 7a and 7b is 22 kHz.

The speakers 9aa, 9ab, 9ba and 9bb are placed within the room 20, which is an acoustically closed sound-shielded room. The speakers 9aa, 9ab, 9ba and 9bb convert the input signals into sounds, respectively, and apply them to a person 30, who is a subject of measurement.

Detection electrodes are provided at, for example, 12 scalp sites of the person 30. An EEG detector and transmitter 32 connected to the detection electrodes converts an EEG detected by each detection electrode into a radio signal and transmits the resulting signal from an antenna 33 toward an antenna 34. The radio signal of the EEG is received by the antenna 34, and is then delivered to an EEG data receiving and recording apparatus 31. In the EEG data receiving and recording apparatus 31, the received radio signal of the EEG is converted into an EEG signal, and is then recorded to a magnetic recorder provided within the EEG data receiving and recording apparatus 31. Further, the EEG signal is analyzed by an analysis computer, while variations in the EEG are recorded and outputted by using an output equipment such as a CRT display, a pen recorder or the like. On the other hand, the head of the person 30 is placed so as to be sandwiched between two detector elements of a detector 42 for the tomograph. A detection signal derived from the detector 42 for the tomograph is transmitted to a tomograph apparatus 41. Subsequently, the tomograph apparatus 41 executes a predetermined tomographical analysis process based on the input detection signal, and displays a tomographical view of the analysis result onto a built-in CRT display of the tomograph apparatus 41.

Figure 26A:
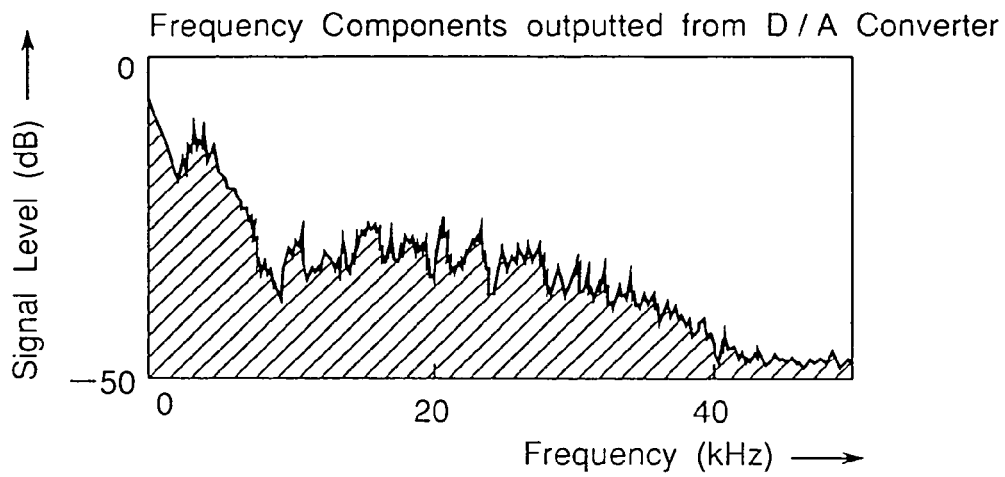
FIGS. 26A, 26B and 26C are graphs showing frequency characteristics of respective signals in the signal sound generating apparatus shown in FIG. 1, where
Figure 26B:
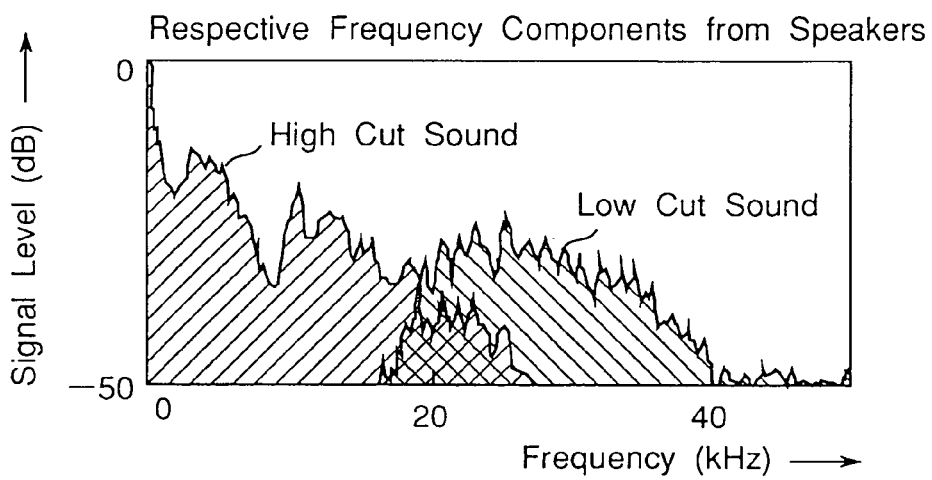
Figure 26C:
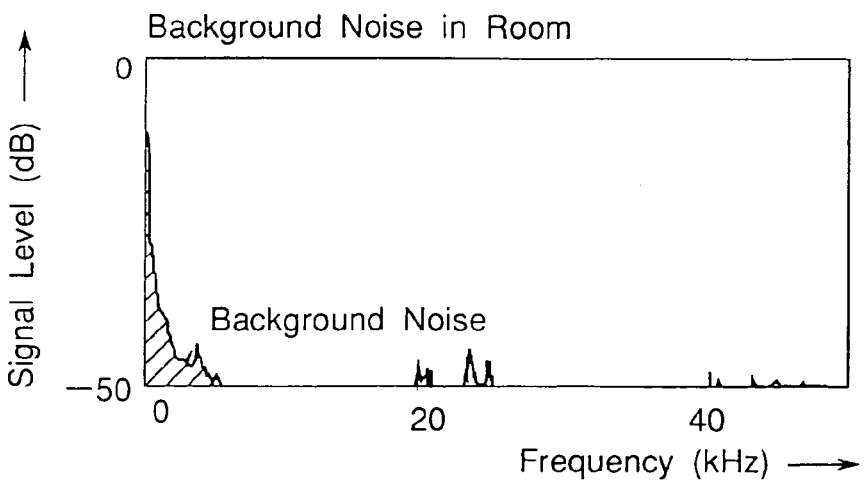

FIGS. 26A, 26B and 26C show frequency characteristics of respective signals in the signal sound generating apparatus of the first preferred embodiment shown in FIG. 1 as constructed above, where FIG. 26A is a graph showing a frequency characteristic of a frequency component outputted from a D/A converter 5 shown in FIG. 1, FIG. 26B is a graph showing frequency characteristics of respective frequency components outputted from the speakers 9aa, 9ab, 9ba and 9bb shown in FIG. 1, and FIG. 26C is a graph showing a frequency characteristic of the background noise in the room 20 shown in FIG. 1

In the signal sound generating apparatus and the room 20 of the first preferred embodiment having the above-mentioned constitution, after the instrumental sounds produced by playing the Gamelan ensemble 1 with both the switches SW1 and SW2 turned on are recorded to the magnetic tape 13 of the magnetic recording and reproducing apparatus 10, and thereafter, when the sound signals are reproduced, the reproduced sound signals substantially identical to the instrumental sounds of the Gamelan ensemble 1 can be applied to the person 30 by using the speakers 9aa, 9ab, 9ba and 9bb. In this case, by turning on or off the switches SW1 and SW2, the instrumental sound signals in various kinds of frequency components can be generated by the speakers 9aa, 9ab, 9ba and 9bb. That is, with only the switch SW1 turned on, signals having only high-frequency components above 22 kHz are applied to the person 30, while with only the switch SW2 turned on, signals having only low-frequency components below 22 kHz are applied to the person 30. In addition, with both the switches SW1 and SW2 turned off, background noise components of the baseline (hereinafter, referred to as background noise components) including (i) aerial vibrations generated by equipments provided in the room 20 and (ii) negligible small noise components due to thermal noise components of the power amplifiers 8a and 8b are applied to the person 30.

The experimental results obtained using the signal sound generating apparatus and the room 20 of the present preferred embodiment are discussed below in detail.

Figure 3:
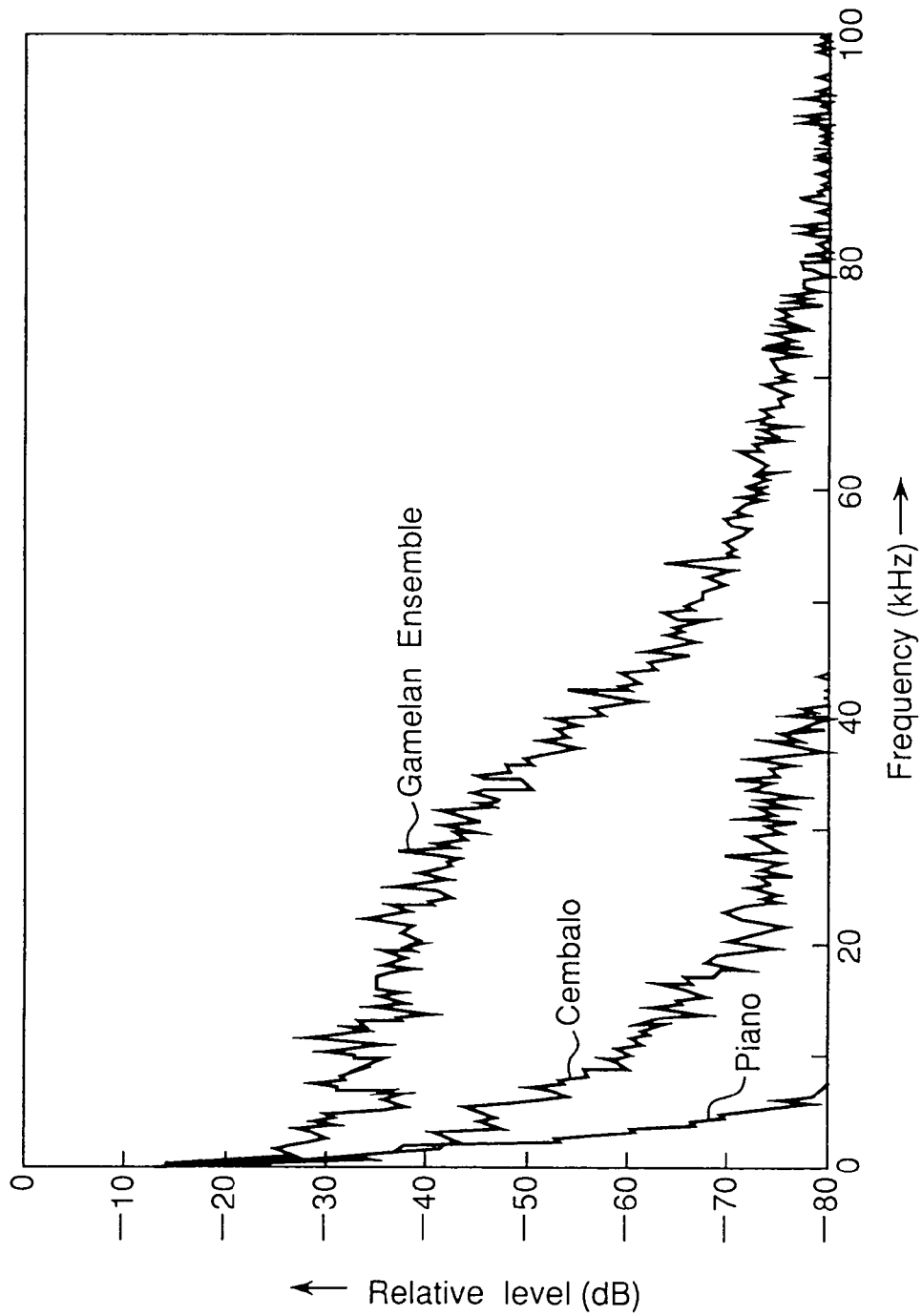
FIG. 3 is a graph showing frequency characteristics of signals produced by the Gamelan ensemble, a cembalo, and a piano used in the preferred embodiments.

FIG. 3 is a graph showing frequency characteristics of signals generated by the Gamelan ensemble, the cembalo, and the piano used in the preferred embodiments. The frequency characteristic shown in FIG. 3 is an averaged power spectrum of each instrumental sound with a duration of 30 seconds. As apparent from FIG. 3, the instrumental sound of the Gamelan ensemble contains frequency components above 100 kHz, and still, although not shown in FIG. 3, the instrumental sound of the Gamelan ensemble instantaneously contains frequency components up to about 150 kHz. Further, the instrumental sound of the cembalo contains frequency components of low-frequency components to about 50 kHz frequency components, while the instrumental sound of the piano contains frequency components up to about 10 kHz.

Figure 4:
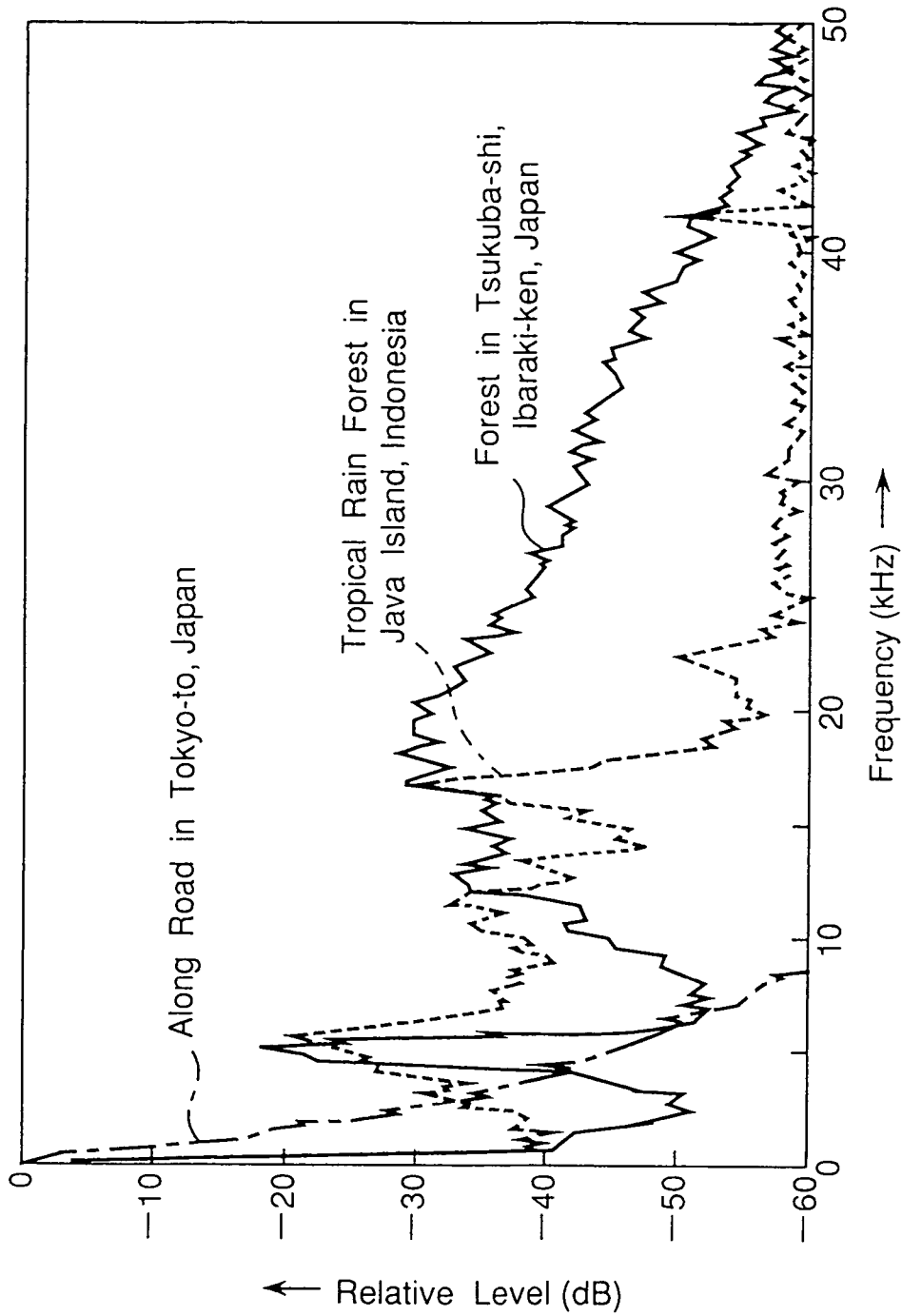
FIG. 4 is a graph showing frequency characteristics of environmental sounds in a forest in Tsukuba-shi, Ibaraki-ken, Japan, in a tropical rain forest in Java Island, Indonesia, and along a road in Tokyo-to, Japan.

FIG. 4 is a graph showing frequency characteristics of environmental sounds in a forest in Tsukuba-shi, Ibaraki-ken, Japan, in a tropical rain forest in Java Island, Indonesia, and along a road in Tokyo-to, Japan. As apparent from FIG. 4, whereas the sound along the road in Tokyo-to has frequency components up to as low as about 8 kHz, the sounds in the forest in Tsukuba-shi and in the rain forest in Java Island have high-frequency and low-frequency components up to about 50 kHz.

Next, the inventors performed digital signal processing to analyze the instrumental sounds of the Gamelan ensemble and the piano recorded with the magnetic recording and reproducing apparatus 10, by using the Maximum Entropy Method (MEM) which has been already publicly known to those skilled in the art. In this analysis process, acoustic signal data of instrumental sounds were sampled with a sampling frequency of 200 kHz, and 2000 pieces of data were obtained in every 20 msec. Then, the MEM spectra of a maximum frequency of 100 kHz were calculated, by which the MEM spectra of FIGS. 5 to 8 were obtained in a time series.

Figure 5:
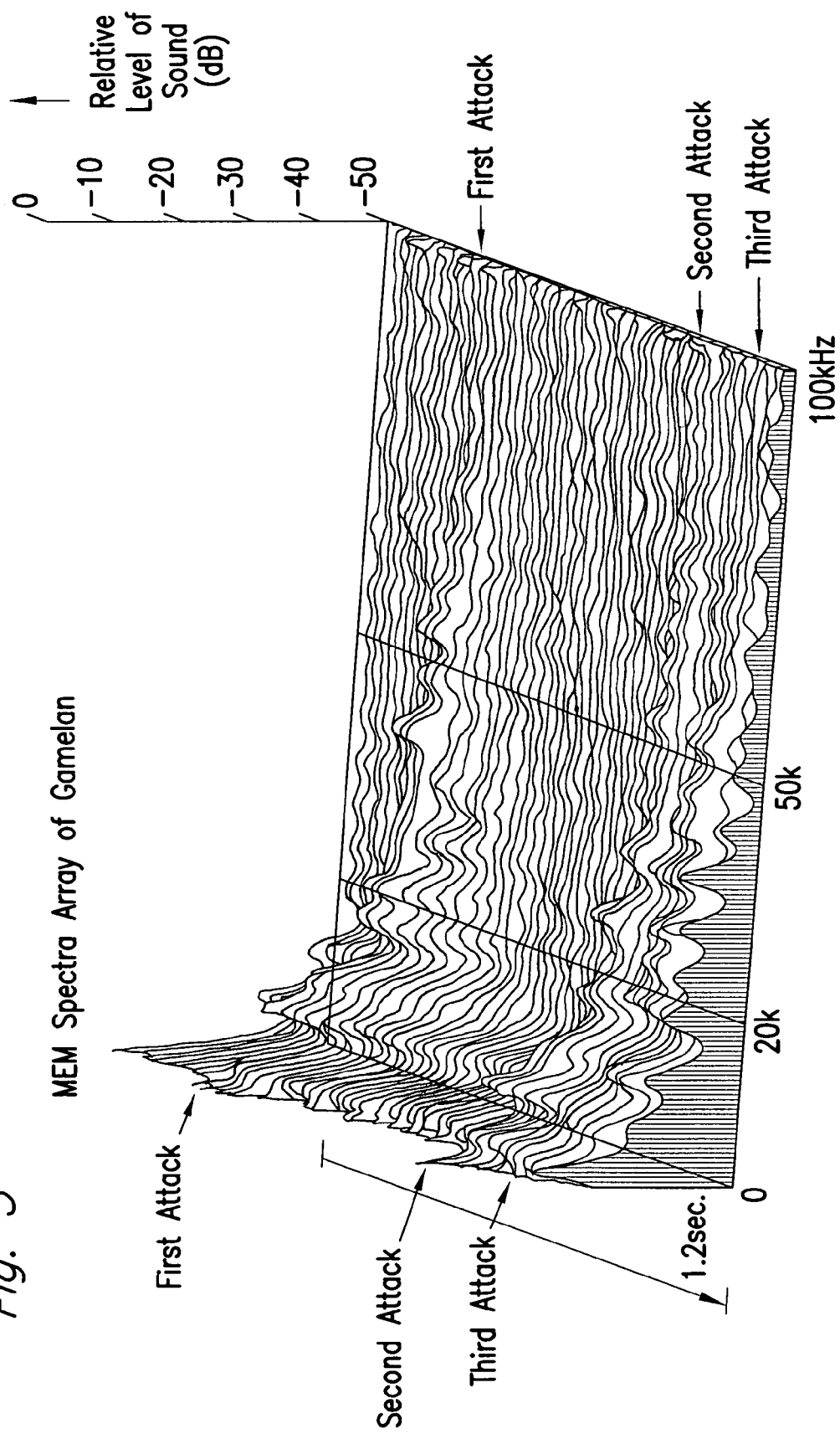
FIG. 5 is a graph showing an MEM spectra array of the Gamelan ensemble sound up to 100 kHz, which is used in the preferred embodiments.
Figure 6:
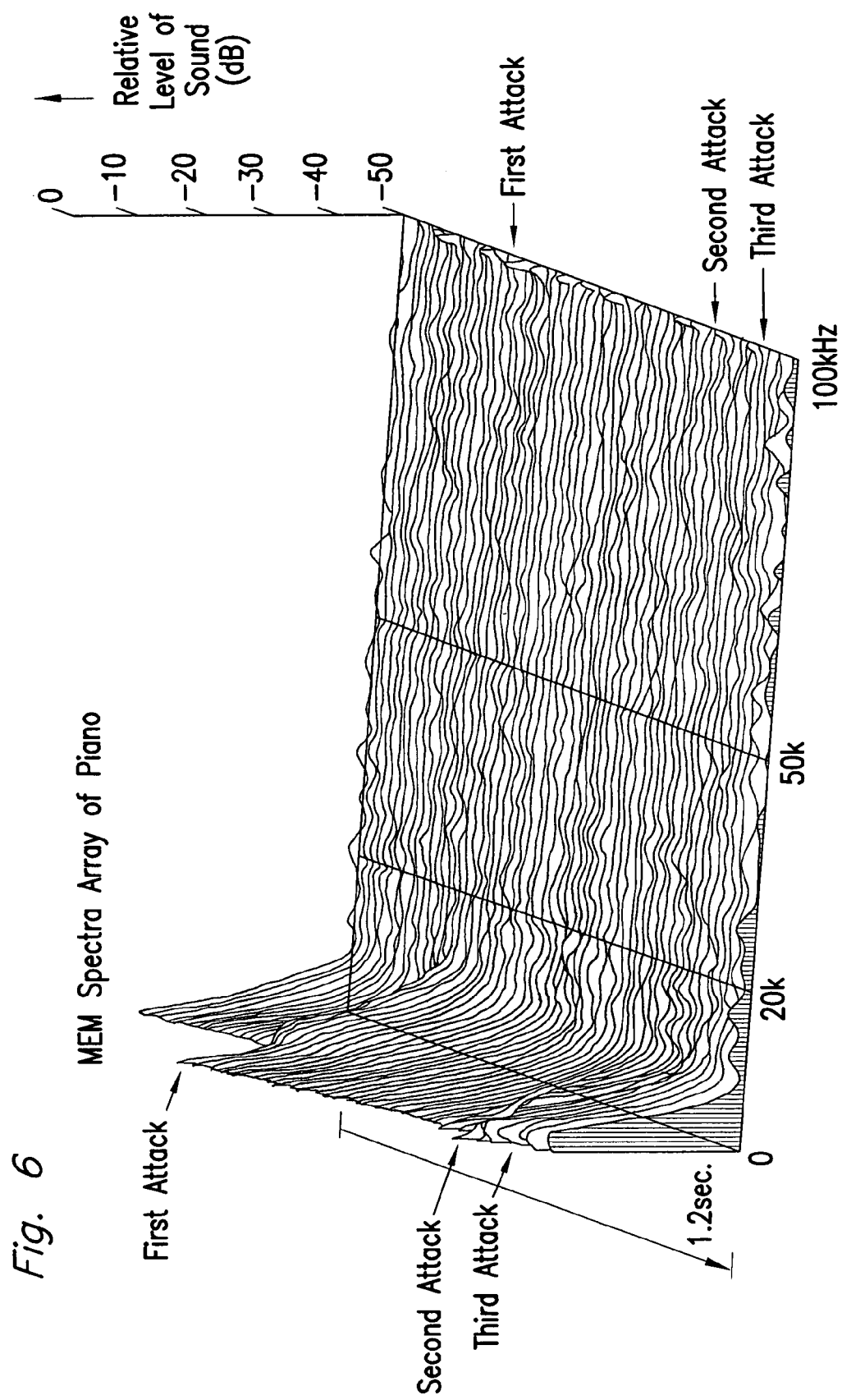
FIG. 6 is a graph showing an MEM spectra array of the piano sound up to 100 kHz, which is a comparative example.

MEM spectra time-series arrays of the same part of the composition "Gambang Kuta" played on both the Gamelan ensemble of the present preferred embodiment and the piano of the comparative example are shown in FIGS. 5 to 8. It should be noted that the Gamelan ensemble music contained dynamic and complex non-stationary structures over 50 kHz with the changes between the frequency spectra as shown in FIG. 5. On the other hand, frequency spectra over 10 kHz were hardly observed in the same music played on the piano as shown in FIG. 6. These results agreed with results from using an FFT analysis.

Figure 7:
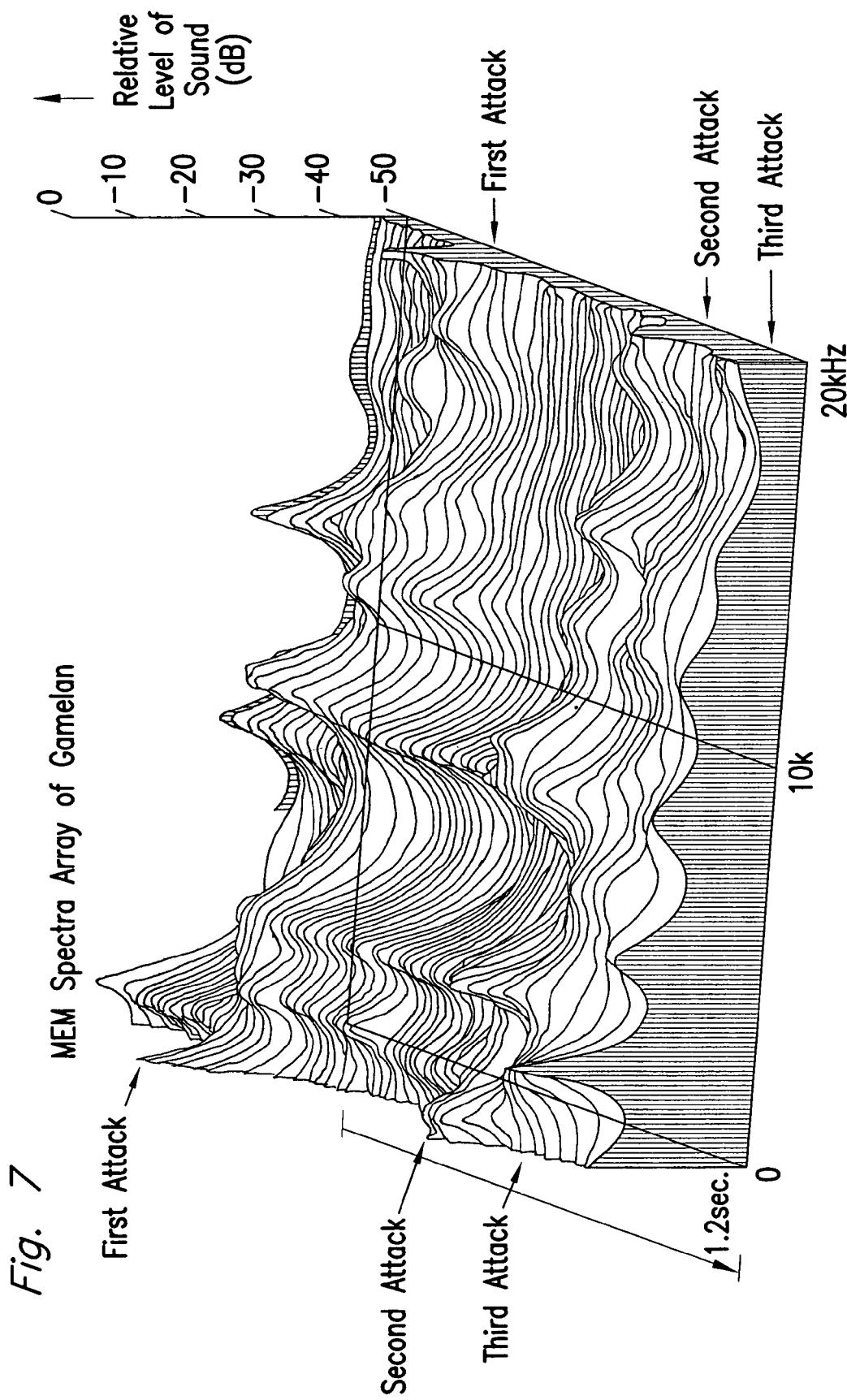
FIG. 7 is a graph showing an MEM spectra array of the Gamelan ensemble sound up to 20 kHz, which is used in the preferred embodiments.
Figure 8:
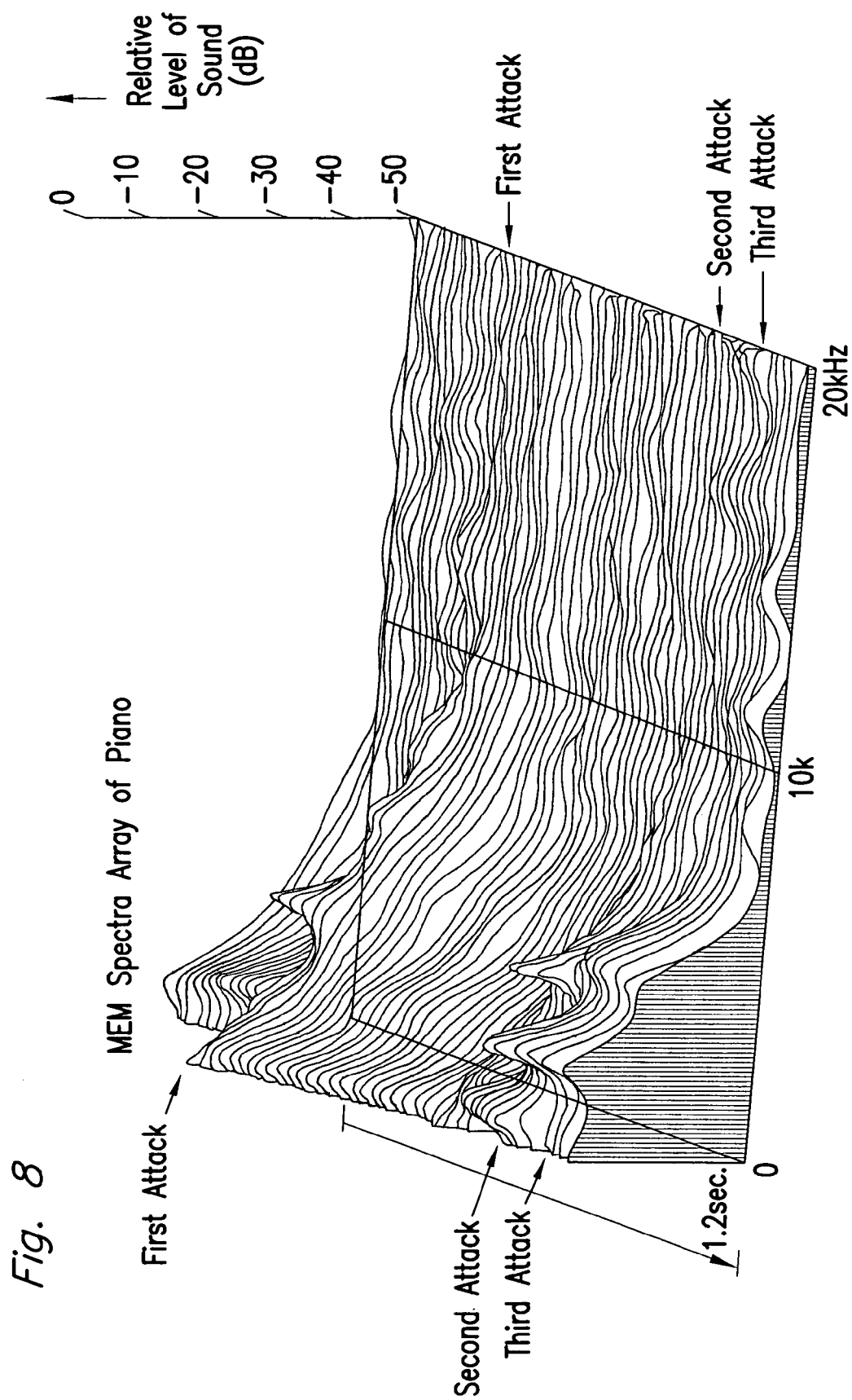
FIG. 8 is a graph showing an MEM spectra array of the piano sound up to 20 kHz, which is a comparative example.

When the player pushed or hit the keys, we indicated as "attack" in FIGS. 5 to 8, where the pattern of MEM spectra changed in both of the Gamelan ensemble and piano music. This seemed to reflect a change of pitch. In the Gamelan ensemble music, the change in the frequency spectra remained for a while, and a fluctuation structure not caused by the change of pitch in the micro-temporal area was observed. In the piano music, the change in the spectra immediately stabilized after the attack. As shown in FIG. 7, the tones of the Gamelan ensemble sounds were observed stationary in the lower frequency range under 10 kHz, however, in the higher frequency range above 10 kHz there were obvious non-stationary structures in the micro-temporal area. In the piano music, as shown in FIG. 8, there was no such tendency of the tones.

As stated above, in the Gamelan ensemble music, a fluctuation structure in the high-frequency range over 50 kHz was observed, which was not caused by the key change. In the piano music, one of the typical musical instruments of the Western classic music, no such fluctuation structure was found. In addition, almost of the Gamelan ensembles are in pairs. In the traditional way of tuning Gamelan instrument, each member of a pair is tuned to a slightly different pitch. It is supposed that this "detuning" technique would be one of the reasons for such a non-stationary structure. Thus, the instrumental sounds of the Gamelan ensemble contain the audible frequency range, for example, from about 20 Hz to about 20 kHz as well as an extremely high frequency range beyond the audible range and up to 150 kHz, and yet there are fluctuations in the micro-temporal area of within 1 sec or $\frac{1}{10}$ sec in the frequency components beyond 10 kHz. That is, in the frequency components, there exists a non-stationary signal sound that changes in the micro-temporal area.

Next discussed are the measurement of regional cerebral blood flow value (hereinafter, referred to as an r-CBF value) and the measurement of α-EEG. In the measurement of r-CBF value, scanning was done with a multi-slice PET scanner PCT3600W made by Hitachi Medical, Tokyo, Japan, indicated by reference numeral 41, for 120 seconds at FWHM (Full Width at Half Maximum) of 9 mm in the transaxial direction and 6.5 mm in the axial direction, by which data of 15 slices with the center-to-center interslice distance of 7 mm were obtained. Now, to the measurement-subject person 30, $^{15}$O-labeled water was injected with an intravenous syringe for 15 seconds by 30 mCi/6 ml, one minute after the playing was started. Images resulting from the tomographical process were examined with the ANALYZE system (BRU, Mayo Foundation, Rochester Minn., U.S.A.), and a statistical analysis was performed with the PROMATLAB system (Math Works, Natick, Mass., U.S.A.) using statistical parametric map (SPM, MRC Cyclotron Unit, United Kingdom).

In FIGS. 10 and 11, which will be shown later, the location of the maximum significant point for each activated area is given by x, y and z referring to the stereotactic coordinates in the three orthogonal dimensions of the atlas by Talairach and Tournoux (referred to as a Talairach coordinates hereinafter).

In the measurement of the EEG, EEGs were measured from 12 scalp sites using linked earlobe electrodes as a reference and using an EEG data receiving and recording apparatus 31 including the WEE-6112 telemetric system (Nippon Koden, Tokyo, Japan). The mean value of each subject was taken as measurement basic data, and an output value obtained by normalizing α-EEG potentials derived from the posterior $\frac{2}{3}$ sites of scalp based on the brain electric activity map (BEAM) was taken as a measurement value. Throughout the following figures, reference character P denotes the significant threshold resulting after Fisher's PLSD post hoc test following ANOVA, meaning the possibility that the same results as obtained here may occur absolutely by chance. Reference character r denotes the correlation function, representing the strength of the relation between increase or decrease of blood flow and increase or decrease of α-EEG potential. The Z score is a value that determines the significant threshold P, representing a gap from the average value of observation values obtained in the standardized whole data distribution.

Normalized r-CBF values and normalized α-EEG potentials were measured in the following five divisions of frequency components for comparison with one another:

(a) Full range sound: frequency components with both the switches SW1 and SW2 turned on;

(b) Low cut sound or High-frequency components: frequency components with only the switch SW1 turned on;

(c) High cut sound or Low-frequency components: frequency components with only the switch SW2 turned on;

(d) only background noise: frequency components with both switches SW1 and SW2 turned off; and (e) Virtual full range sound (See FIGS. 14 and 15): frequency components including the high cut sound, and virtual, stationary low cut sounds which are obtained by filtering and waveform-shaping the electronically generated stationary white noise by approximating them to the time-average frequency spectrum of the low cut sounds and which have no fluctuation structures that change in the micro-temporal area in a frequency range beyond 10 kHz.

Figure 27:
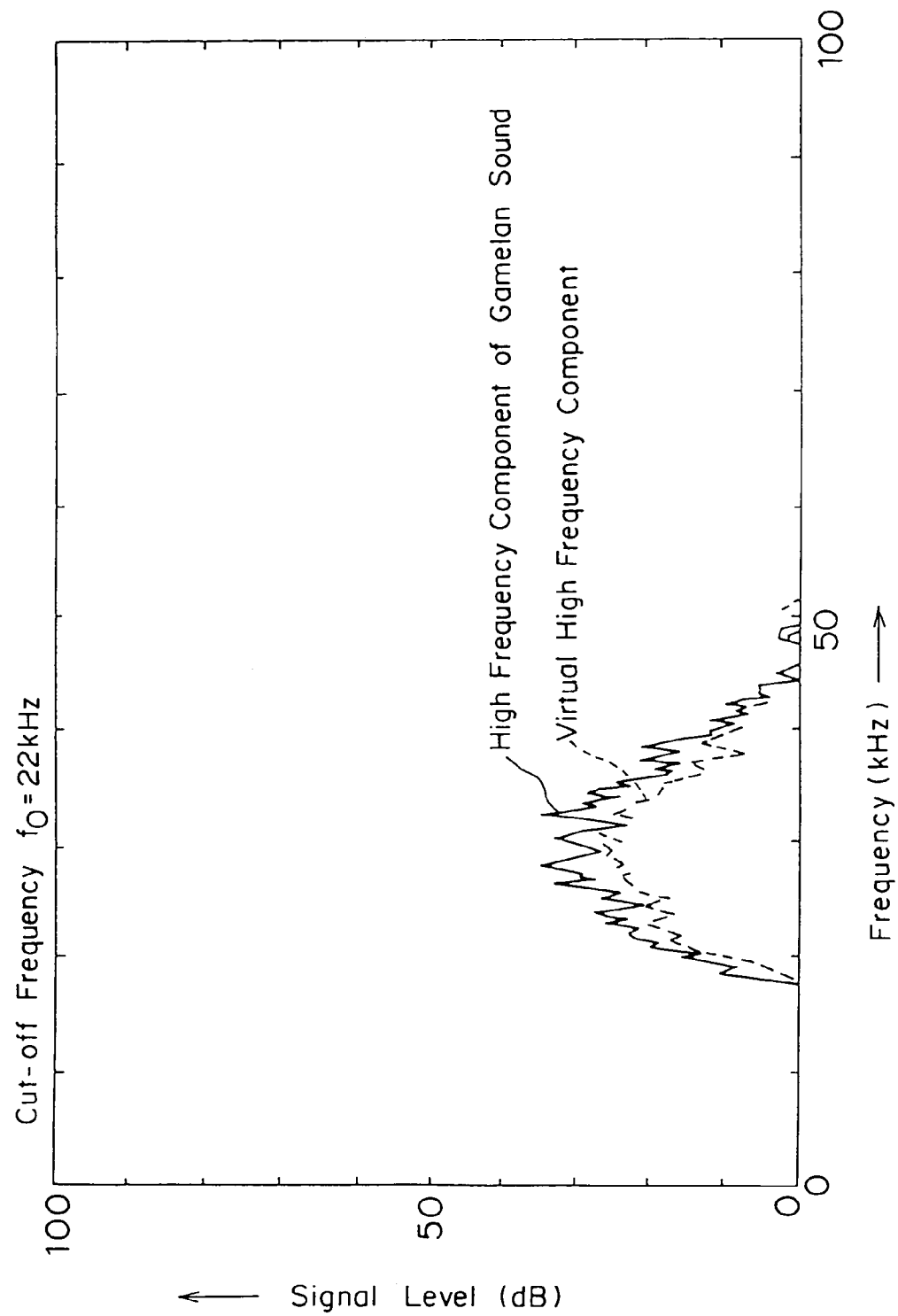
FIG. 27 is a graph showing respective frequency characteristics of (i) a high frequency component of a Gamelan ensemble sound used in the signal sound generating apparatus shown in FIG. 1, and (ii) a virtual stationary high frequency component not having any fluctuation structure, changing in the micro-temporal in the frequency range above 10 kHz, which is obtained by filtering and waveform-shaping a stationary white noise electrically generated so that the stationary white noise approximates to time-averaged spectral of the temporal component of (i) the high frequency component.

FIG. 27 shows respective frequency characteristics of (i) a high frequency component of a Gamelan ensemble sound used in the signal sound generating apparatus shown in FIG. 1, and (ii) a virtual stationary high frequency component not having any fluctuation structure, changing in the micro-temporal area in the frequency range above 10 kHz, which is obtained by filtering and waveform-shaping a stationary white noise electrically generated so that the stationary white noise approximates to time-averaged spectral of the temporal component of (i) the high frequency component.

Figure 16A:
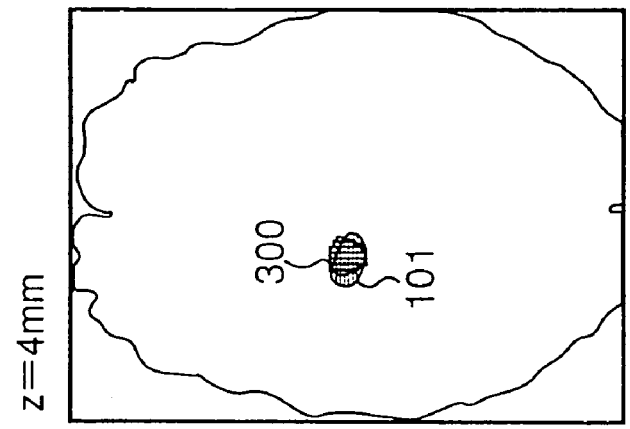
FIGS. 16A, 16B and 16C are transversal cross sectional views for different z's of the Talairach coordinates in the first preferred embodiment, showing a part in which the α-EEG potential significantly correlates with the r-CBF value, as well as a part in which the cerebral blood flow significantly increases, where
Figure 16B:
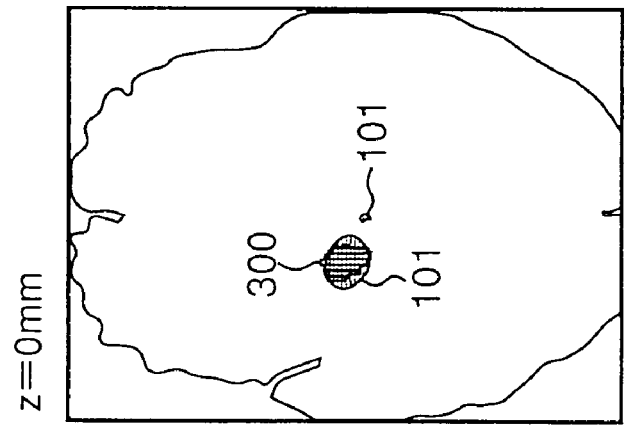
Figure 16C:
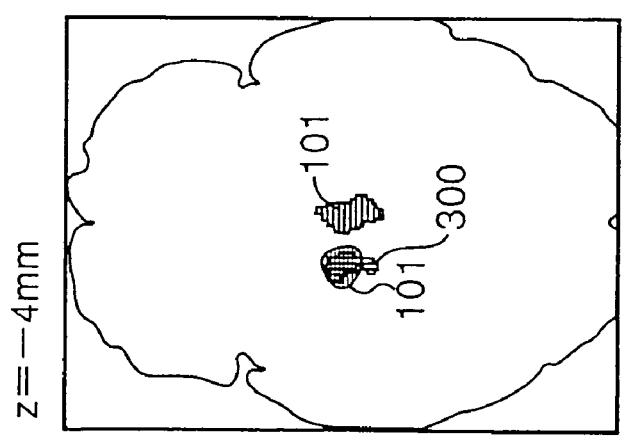
Figure 17:
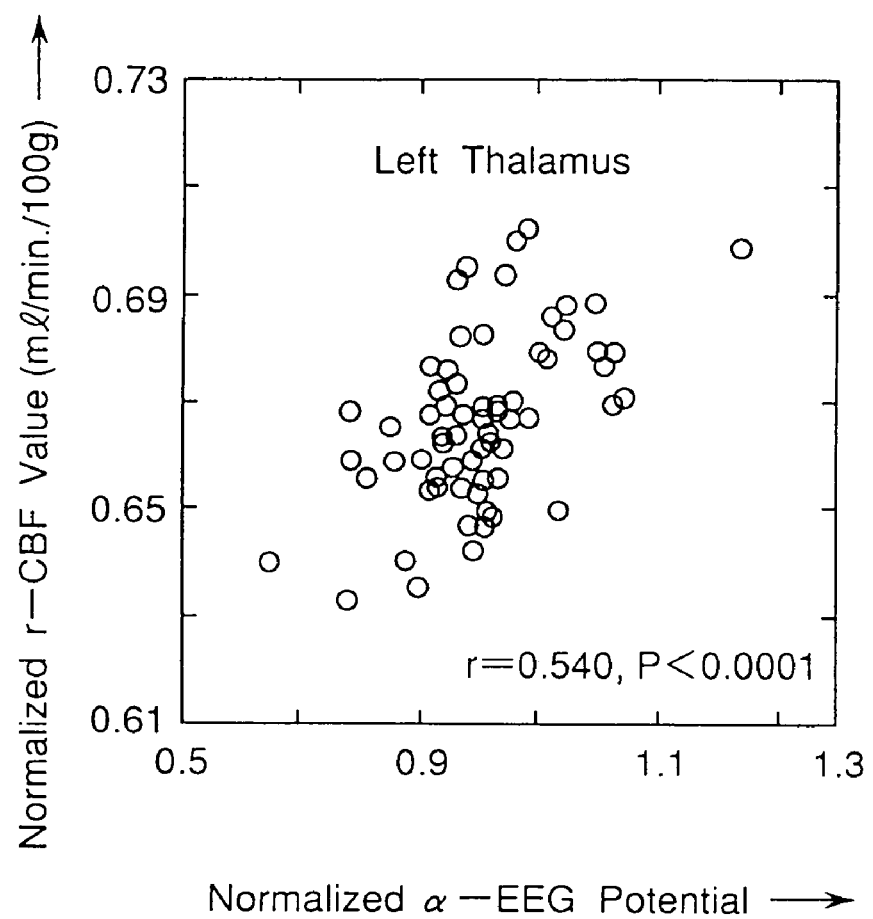
FIG. 17 is a graph showing a correlation between r-CBF values and normalized α-EEG potentials at the position of the left thalamus in the first preferred embodiment.

Furthermore, in the correlation analysis between α-EEG potentials and r-CBF values as shown in FIGS. 16 and 17, normalized α-EEG potentials and r-CBF values in the activated objective sites were examined.

Figure 9A:
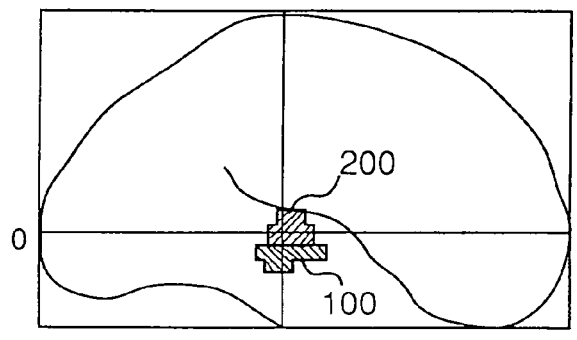
FIGS. 9A, 9B and 9C are projections showing parts of the brain in which cerebral blood flows significantly increase in the full range sound as compared with that in the high cut sound alone in the first preferred embodiment, where
Figure 9B:
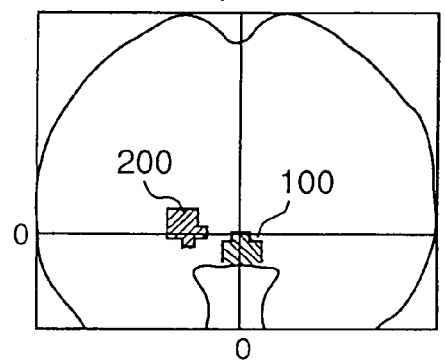
Figure 9C:
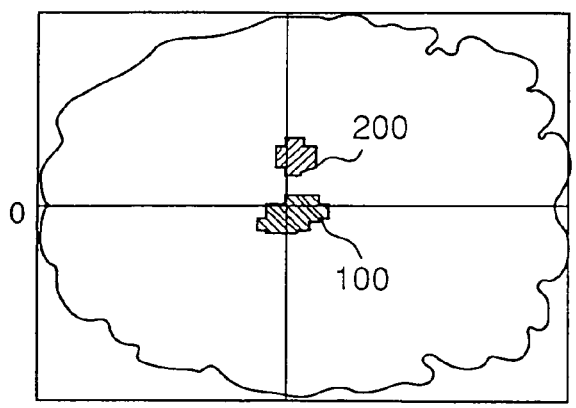

FIGS. 9A, 9B and 9C are projections showing a part 100 of the Talairach coordinates (x, y, z)=(4 mm, −26 mm, −8 mm) corresponding to the brainstem and a part 200 of the Talairach coordinates (x, y, z)=(−16 mm, −18 mm, 0 mm) corresponding to the left thalamus, in which the cerebral blood flows significantly increase in the full range sound as compared with that in the high cut sound alone in the first preferred embodiment, where FIG. 9A shows a sagittal projection which is a projection along the sagittal suture of the human skull, FIG. 9B is a coronal projection which is a projection along the coronal suture of the skull, and FIG. 9C is a transversal projection of the skull. As apparent from FIGS. 9A, 9B and 9C, it can be seen that the cerebral blood flows significantly increase in the brainstem and the left thalamus when the full range sound is applied to the subject person 30, as compared with that when only the high cut sound is applied.

Figure 10A:
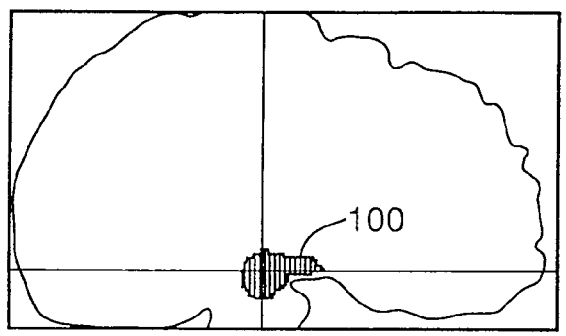
FIGS. 10A, 10B and 10C are sectional views respectively corresponding to FIGS. 9A, 9B and 9C in the first preferred embodiment, and showing a part of the brainstem in which the cerebral blood flow significantly increases in the full range sound as compared with that in the high cut sound alone, where
Figure 10B:
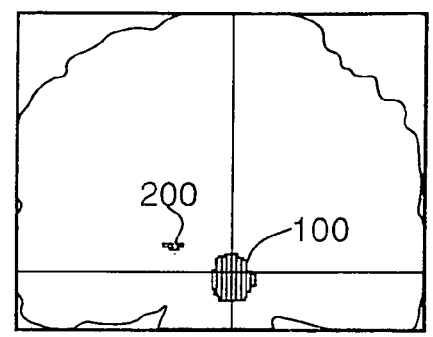
Figure 10C:
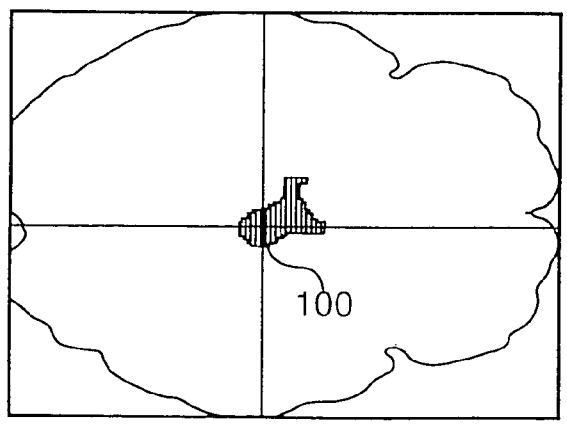
Figure 11A:
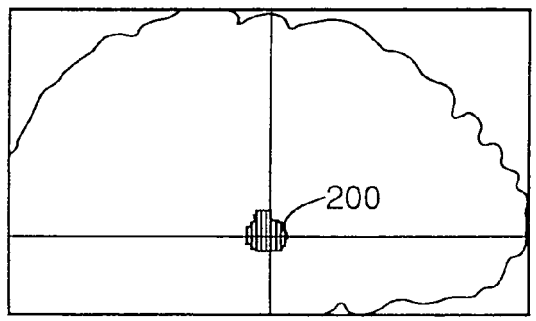
FIGS. 11A, 11B and 11C are sectional views respectively corresponding to FIGS. 9A, 9B and 9C in the first preferred embodiment, and showing parts of a left thalamus in which cerebral blood flows significantly increase in the full range sound as compared with that in the high cut sound alone, where
Figure 11B:
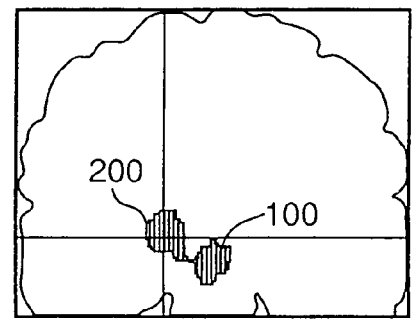
Figure 11C:
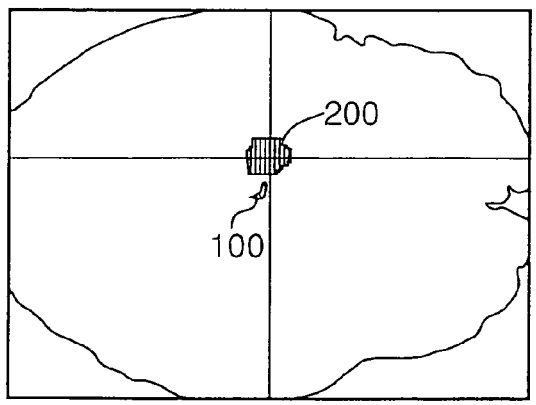

FIGS. 10A, 10B and 10C are sectional views respectively corresponding to FIGS. 9A, 9B and 9C in the first preferred embodiment, and showing a part 100 of the brainstem in which the blood flow significantly increases in the full range sound as compared with that in the high cut sound alone, where FIG. 10A is a longitudinal sectional view showing a sagittal cross section along the sagittal suture of the human skull, FIG. 10B is a longitudinal sectional view showing a coronal cross section along the coronal suture of the skull, and FIG. 10C is a transversal cross sectional view of the skull. FIGS. 11A, 11B and 11C are sectional views respectively corresponding to FIGS. 9A, 9B and 9C in the first preferred embodiment, and showing the part 200 of the left thalamus in which the cerebral blood flow significantly increases in the full range sound as compared with that in the high cut sound alone, where FIG. 11A is a longitudinal sectional view showing a sagittal cross section along the sagittal suture of the human skull, FIG. 11B is a longitudinal sectional view showing a coronal cross section along the coronal suture of the skull, and FIG. 11C is a transversal cross sectional view of the skull.

As apparent from FIGS. 10A, 10B and 10C and FIGS. 11A, 11B and 11C, it can be seen that the cerebral blood flows significantly increase in the brainstem and the left thalamus when the full range sound is applied to the subject person 30, as compared with that when only the high cut sound is applied.

Figure 12A:
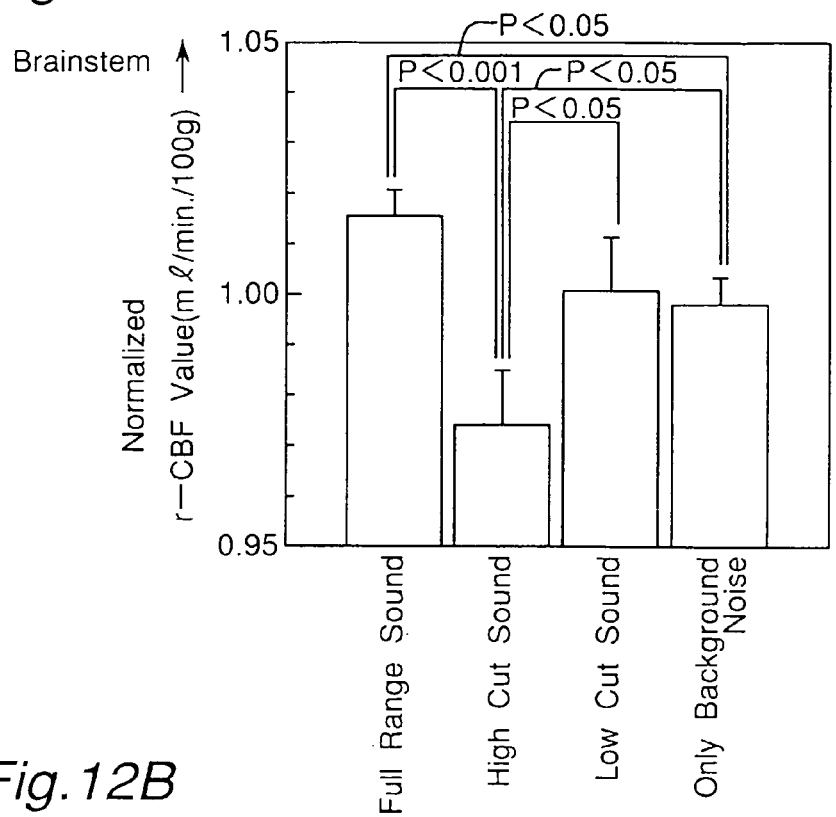
FIGS. 12A and 12B are graphs showing normalized r-CBF values for the respective sounds in the first preferred embodiment, where
Figure 12B:
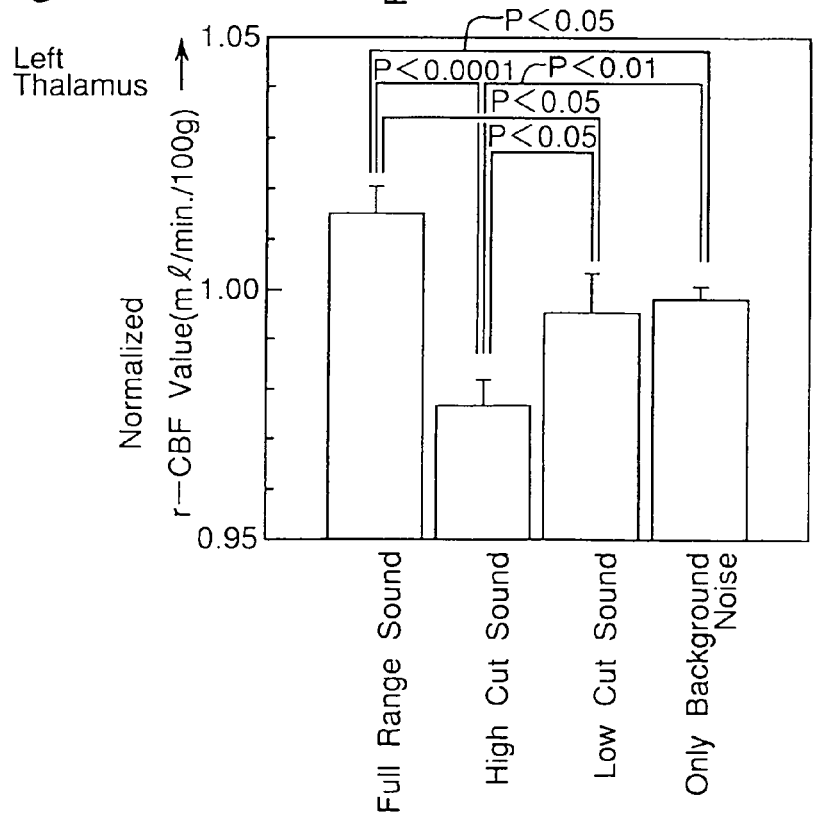

FIGS. 12A and 12B are graphs showing normalized r-CBF values for the respective sounds in the first preferred embodiment, where FIG. 12A is a graph showing the r-CBF values at the brainstem, and FIG. 12B is a graph showing the r-CBF values at the left thalamus.

As apparent from FIG. 12A, it can be seen that the r-CBF value at the position of the brainstem increases and the cerebral blood flow increases at the position of the brainstem when the full range sound is applied to the subject person 30, as compared with that when only the high cut sound, only the low cut sound, or only the background noise is applied. As apparent from FIG. 12B, it can also be seen that the r-CBF value at the position of the left thalamus increases and the cerebral blood flow increases at the position of the left thalamus when the full range sound is applied to the subject person 30, as compared with that when only the high cut sound, or only the low cut sound, or only the background noise is applied.

Figure 13:
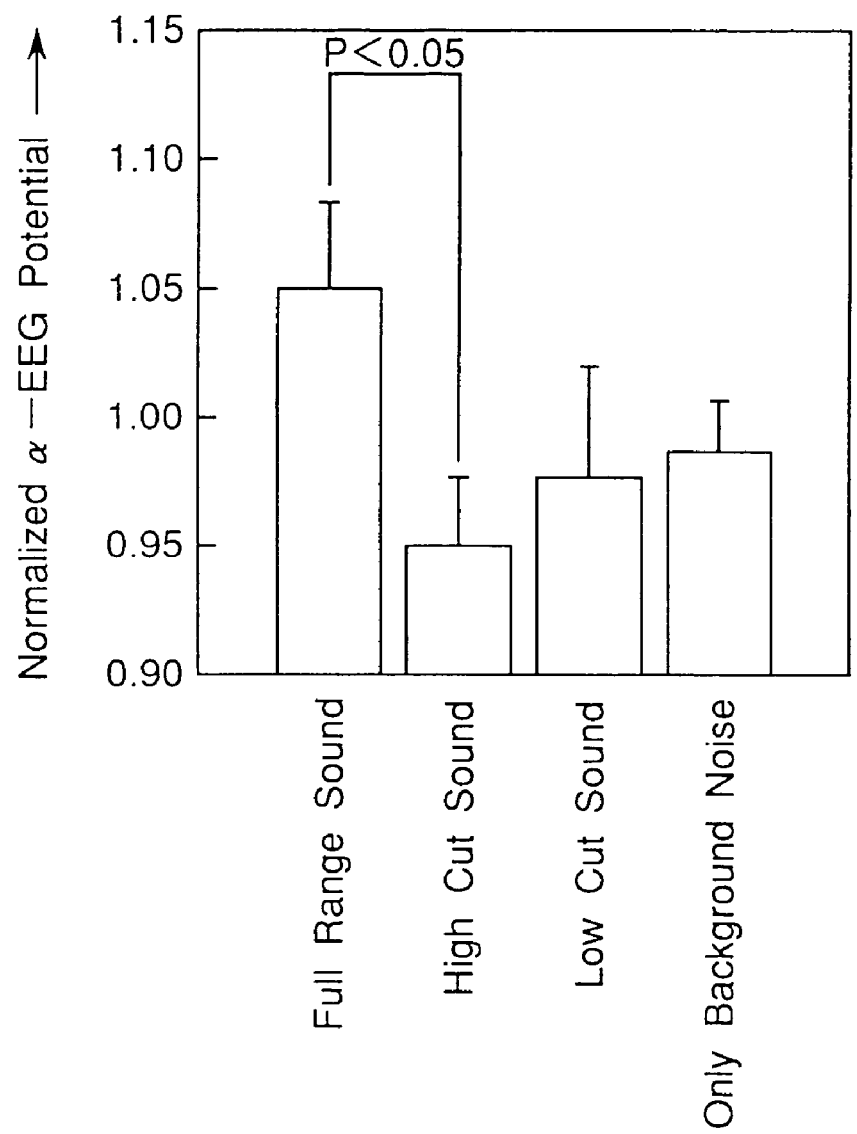
FIG. 13 is a graph showing normalized α-EEG potentials for the respective sounds in the first preferred embodiment.

FIG. 13 is a graph showing normalized α-EEG potentials for the respective sounds in the first preferred embodiment. As apparent from FIG. 13, it can be seen that the α-EEG potential increases when the full range sound is applied to the subject person 30, as compared with that when only the high cut sound, only the low cut sound, or only the background noise is applied.

Figure 14A:
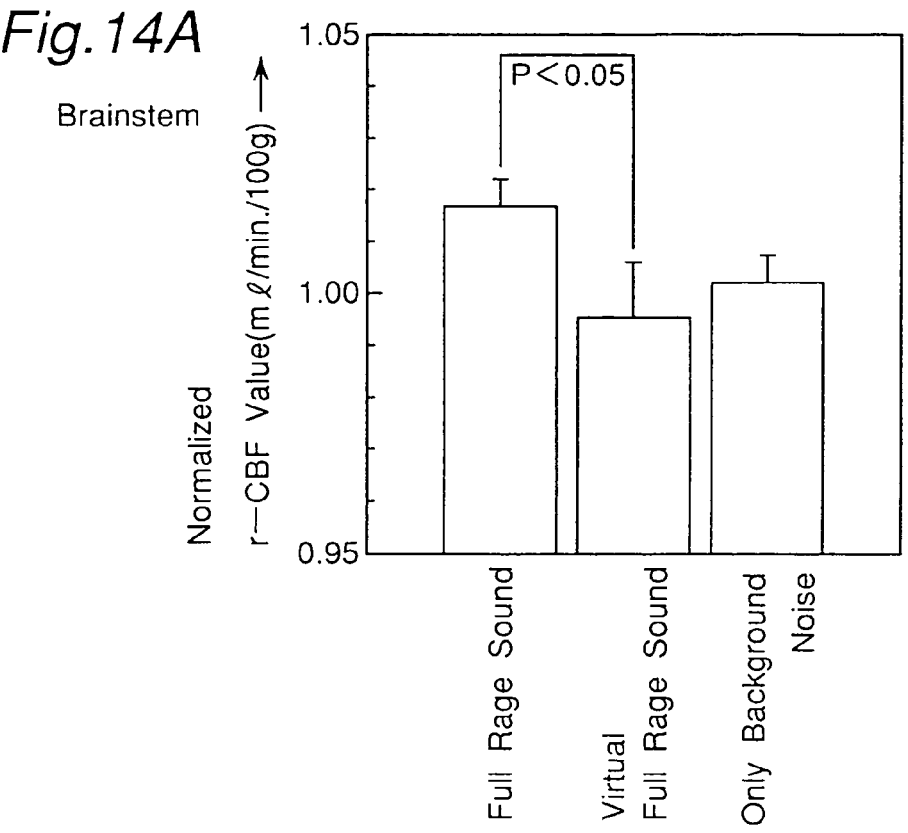
FIGS. 14A and 14B are graphs showing normalized r-CBF values for the respective sounds in the first preferred embodiment, where
Figure 14B:
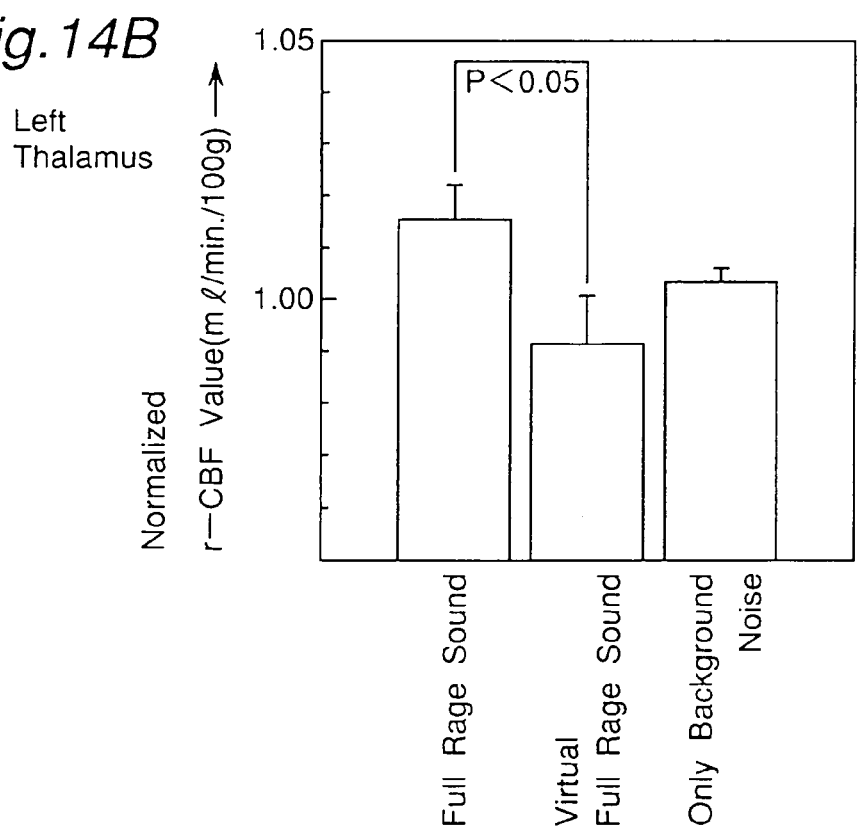

FIGS. 14A and 14B are graphs showing normalized r-CBF values for the respective sounds in the first preferred embodiment, where FIG. 14A is a graph showing the r-CBF values at the brainstem, and FIG. 14B is a graph showing the r-CBF values at the left thalamus. As apparent from FIGS. 14A and 14B, it can be seen that the r-CBF values at the positions of (a) the brainstem and (b) the left thalamus increase and the cerebral blood flows increase at (a) the brainstem and (b) the left thalamus when the full range sound is applied, as compared with that when only the virtual full range sound having no fluctuation structures that change in the micro-temporal area in a frequency range beyond 10 kHz or only the background noise is applied. In contrast to this, it can be seen that when the virtual full range sound having no fluctuation structures that change in the micro-temporal area in a frequency range beyond 10 kHz is applied, the r-CBF values decrease at (a) the brainstem and (b) the left thalamus and the cerebral blood flows decrease at (a) the brainstem and (b) the left thalamus, as compared with that when the full range sound is applied and when the baseline background noise is applied.

Figure 15:
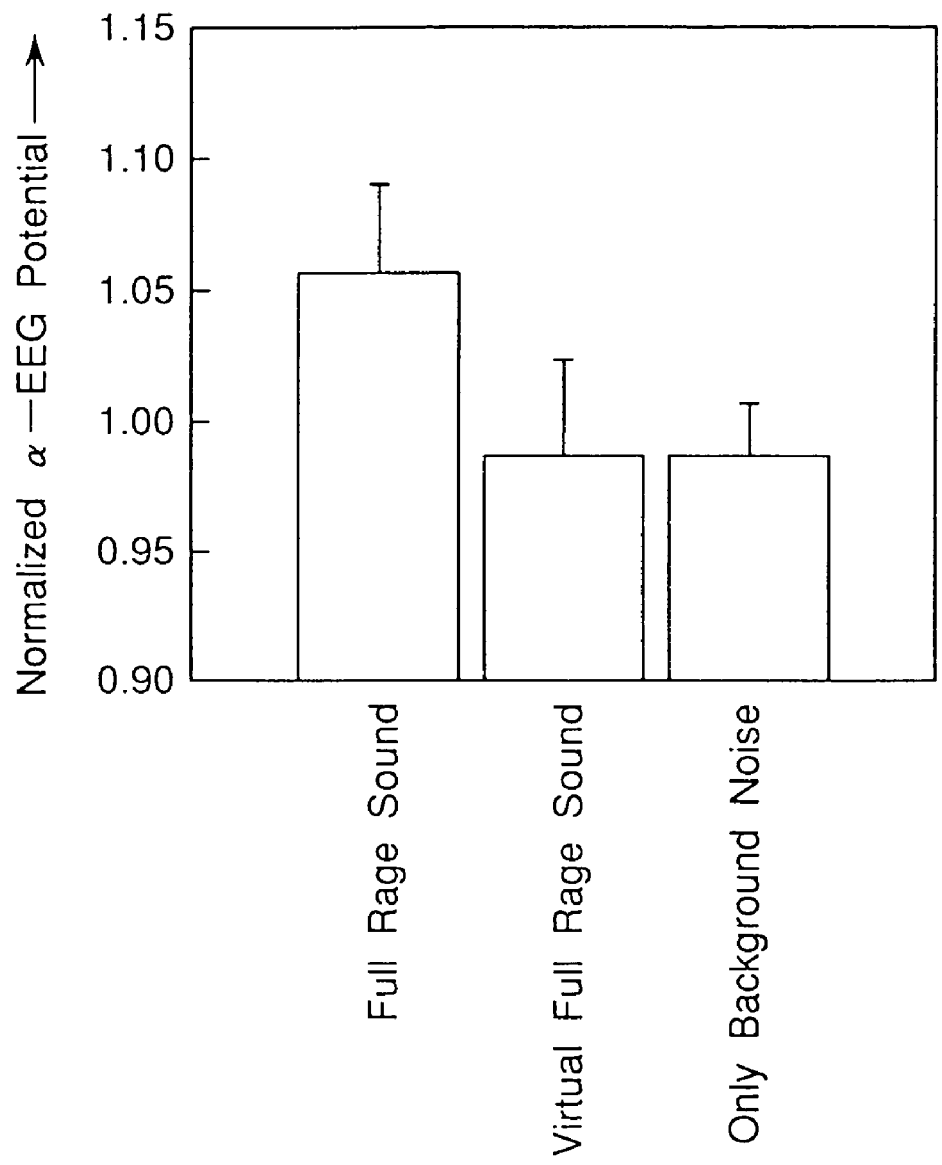
FIG. 15 is a graph showing normalized α-EEG potentials for the respective sounds in the first preferred embodiment.

FIG. 15 is a graph showing normalized α-EEG potentials for the respective sounds in the first preferred embodiment. As apparent from FIG. 15, it can be seen that the α-EEG potential increases when the full range sound is applied to the subject person 30, as compared with that when only the virtual full range sound having no fluctuation structures that change in the micro-temporal area in a frequency range beyond 10 kHz, or only the background noise is applied. In contrast to this, even if the virtual full range sound is applied, the α-EEG potential does not increase, as compared with that when the baseline background noise is applied.

FIGS. 16A, 16B and 16C are transversal views for different z's of the Talairach coordinates, showing a part in which the α-EEG potential significantly correlates with the r-CBF value, as well as a part in which cerebral blood flow significantly increases, where FIG. 16A shows the cross section for z=−4 mm, FIG. 16B shows the cross section for z=0 mm, and FIG. 16C shows the cross section for z=4 mm.

As apparent from FIGS. 16A, 16B and 16C, the part 300 in which the α-EEG potential significantly correlates with the r-CBF value, and the part 101 in which the cerebral blood flow significantly increases are located so as to generally overlap each other at the left thalamus, and this proves that the α-EEG potential increases as the cerebral blood flow increases at the position of the left thalamus.

FIG. 17 is a graph showing a correlation between r-CBF values and normalized α-EEG potentials at the position of the left thalamus in the first preferred embodiment. As apparent from FIG. 17, as the α-EEG potential increases, the r-CBF value increases, and this proves that there is a positive correlation therebetween and their significant thresholds are very close to each other. That is, it can be seen that the α-EEG potential increases when the cerebral blood flow increases at the left thalamus.

The cerebral thalamus is an aggregate of neuronal nuclei located in the depth of the brain, playing an important role as a basis for processing sensory input signals from the whole body including the audio and visual sensations, and for relaying them to the cerebral cortex. The thalamus plays another important role as a key basis which receives and integrates signals derived from the cerebral cortex or the limbic system, and which administrates the control systems of the whole body, such as the internal secretion system and the autonomic nervous system, via the hypothalamus, thus having a close relation to the control of relaxation and stresses that allows one's strains to be alleviated. The thalamus has been also received attention as one of the candidates for the pacemaker of α-EEG that is widely known as an index of relaxed state. Further, the thalamus, which forms the part of the limbic system, is reported that its regional cerebral blood flow value increases in conjunction with emotional variations. According to recent studies, it is reported that in many of schizophrenia patients, regional abnormalities can commonly be seen at the outer part of the thalamus, with an account that various kinds of symptoms of schizophrenia take place as the function of the thalamus is impaired. Thus, in order to relieve one's strains, and then dissipate stresses, thereby relaxing him or her, so that the state of his or her mind and body is enhanced or that these conditions are maintained successfully, it is considerably effective to increase the blood flows of the thalamus, thereby enhancing its activity.

The brainstem has a concentrated distribution of centers of most important life functions having direct relations to the support of life such as breathing, blood pressure, blood sugar control or the like. The evaluation of the activity of the brainstem is the decisive key to the decision of brain death. Further, the brainstem also has the center of the autonomic nervous system which controls the activities of the internal organs of the whole body, the centers of the fundamental actions for living things such as ingestion and sexual actions, the centers of the circadian period such as sleeping and awakening, and the like, and the like. As to the activity level of the whole brain, it is considered that the reticular activating system of the brainstem has a function of controlling the activity level. Furthermore, important neuronal pathways of monoaminergic systems which are distributed to the whole brain, including the medial forebrain bundle (MFB) where neural networks for pleasant feelings and awakening, are derived from the neuronal nuclei of the brainstem, and thought to play an important role for the emotional function. Thus, increasing the blood flows of the brainstem to enhance its activity is considerably effective to enhance the comfortability of human mind as well as the health of human body or to maintain those successful.

By hearing or listening to the instrumental sounds of the Gamelan ensemble, it is enabled to set a quasi-natural comfortable environment. As shown in FIG. 4, by applying low cut sounds beyond the audible frequency range that significantly lack in the sound environments of today's cities, it is enabled to increase the blood flows of the left thalamus and/or the brainstem, to lead the human brain to a α-EEG-dominant state free from stresses, and thus to obtain a hyper sonic effect of more comfortable auditory sensation. As a result, the strains of the person 30 can be relieved so that he or she can be relaxed, stresses can be dissipated, the comfortability of the mind can be enhanced, and the physical health can be maintained successful.

As described above, when a sound which includes the audible frequency range up to 20 kHz as well as an extremely high frequency range beyond the audible range and up to 150 kHz, and yet which has fluctuations present in the micro-temporal area within 1 second or $1/10$ second in frequency components beyond 10 kHz. That is, when the sounds in which there exist non-stationary signal sounds changing in the micro-temporal area in the frequency components, are applied to the person 30, the α-EEG potential can be increased, strains of the person 30 can be relieved so that the person 30 can be relaxed and his or her stresses can be dissipated, and thus the person 30 can be enhanced in the comfortability of the mind and maintained successful in the physical health.

Second Preferred Embodiment

Figure 2:
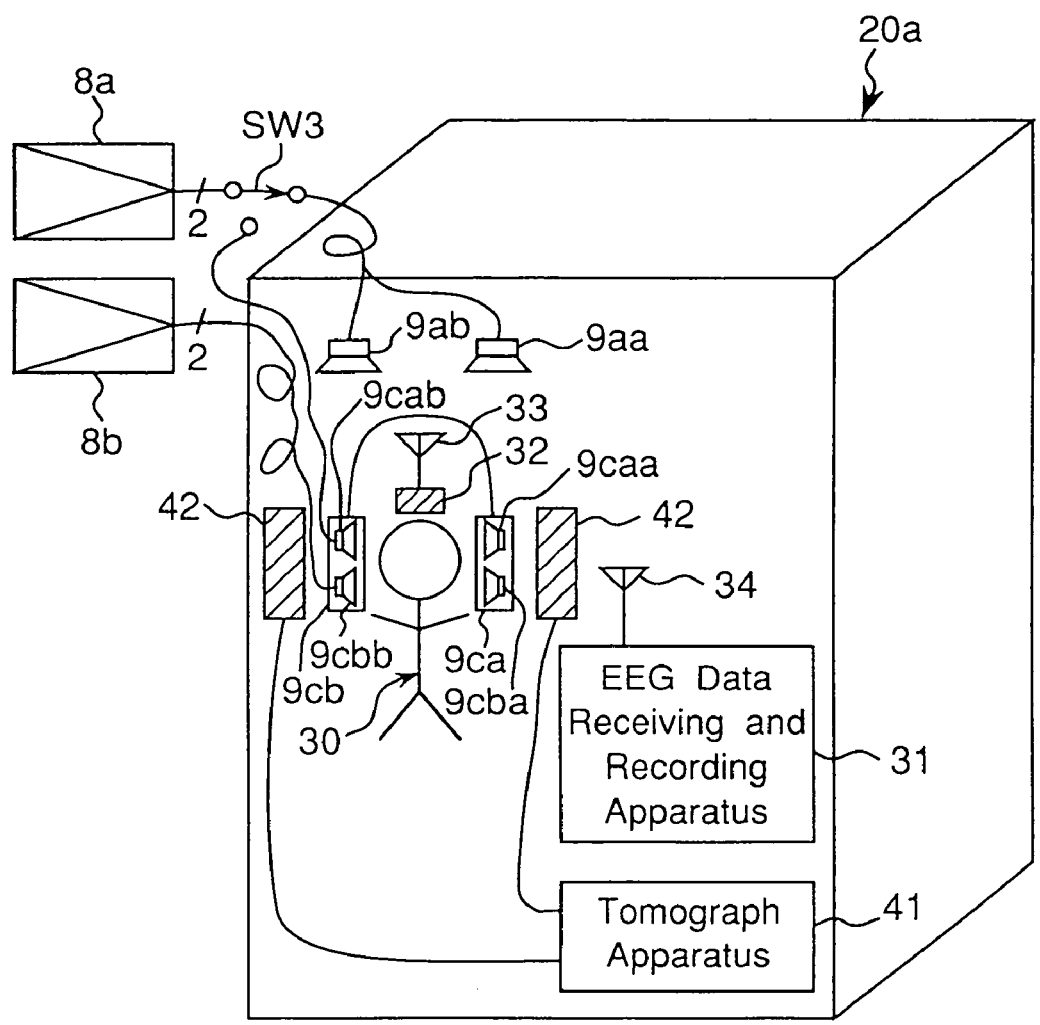
FIG. 2 is a partial block diagram of a signal sound generating apparatus of a second preferred embodiment according to the invention, and a perspective view showing a room for generating signals by the signal sound generating apparatus.

FIG. 2 is a partial block diagram of a signal sound generating apparatus of a second preferred embodiment according to the invention, and a perspective view showing a room 20a for generating signals by the signal sound generating apparatus. In FIG. 2, only the arrangements inside the room 20a different from the first preferred embodiment are shown. Accordingly, the arrangement including and before the power amplifiers 8a and 8b is the same as in the first preferred embodiment.

In the second preferred embodiment, within the room 20a, a right speaker 9aa and a left speaker 9ab are provided, while a right earphone 9ca and a left earphone 9cb for applying instrumental sounds to only the auditory sensation of the person 30 are inserted and mounted into the right and left ears of the person 30, respectively. The right earphone 9ca comprises a low cut sound generator 9caa which is connected to the right output terminal of the power amplifier 8a and which generates low cut sounds above 22 kHz, and a high cut sound generator 9cba which is connected to the right output terminal of the power amplifier 8b and which generates high cut sounds below 22 kHz. On the other hand, the left earphone 9cb comprises a low cut sound generator 9cab which is connected to the left output terminal of the power amplifier 8a and which generates low cut sounds above 22 kHz, and a high cut sound generator 9cbb which is connected to the left output terminal of the power amplifier 8b and which generates high cut sounds below 22 kHz. This system is provided in two systems of the same specifications, as that in the first preferred embodiment, and is used in the so-called stereophonic state in a manner similar to that of the first preferred embodiment. A low cut sound output signal from the power amplifier 8a is outputted to the speakers 9aa and 9ab via a switch SW3 while it is outputted to the low cut sound generators 9caa and 9cab of the earphones 9ca and 9cb via the switch SW3. On the other hand, a high cut sound output signal from the power amplifier 8b is outputted to the high cut sound generators 9cba and 9cbb of the earphones 9ca and 9cb. Accordingly, in the second preferred embodiment, low cut sounds above 22 kHz and/or high cut sounds below 22 kHz can be applied to only the auditory sensation of both ears of the person 30 while low cut sounds above 22 kHz can be applied to the whole person 30.

In the measurement of r-CBF value of the second preferred embodiment, scanning was done with a multi-slice PET scanner of Advance type made by GE Yokogawa Medical, indicated by reference numeral 41, for 90 seconds at FWHM (Full Width at Half Maximum) of 4.2 mm in the transaxial direction and 4.2 mm in the axial direction, by which data of 35 slices with the center-to-center interslice distance of 4.25 mm were obtained. Now, to the measurement-subject person 30, $^{15}$O-labeled water was injected with an automatic intravenous syringe for 40 seconds by 10 mCi/10 ml, at the same time when the playing was started. Images resulting from the tomographical process were examined with the ANALYZE system (BRU, Mayo Foundation, Rochester Minn., U.S.A.), and a statistical analysis was performed with the PROMATLAB system (Math Works, Natick, Mass., U.S.A.) using statistical parametric map (SPM, MRC Cyclotron Unit, United Kingdom).

Figure 18:
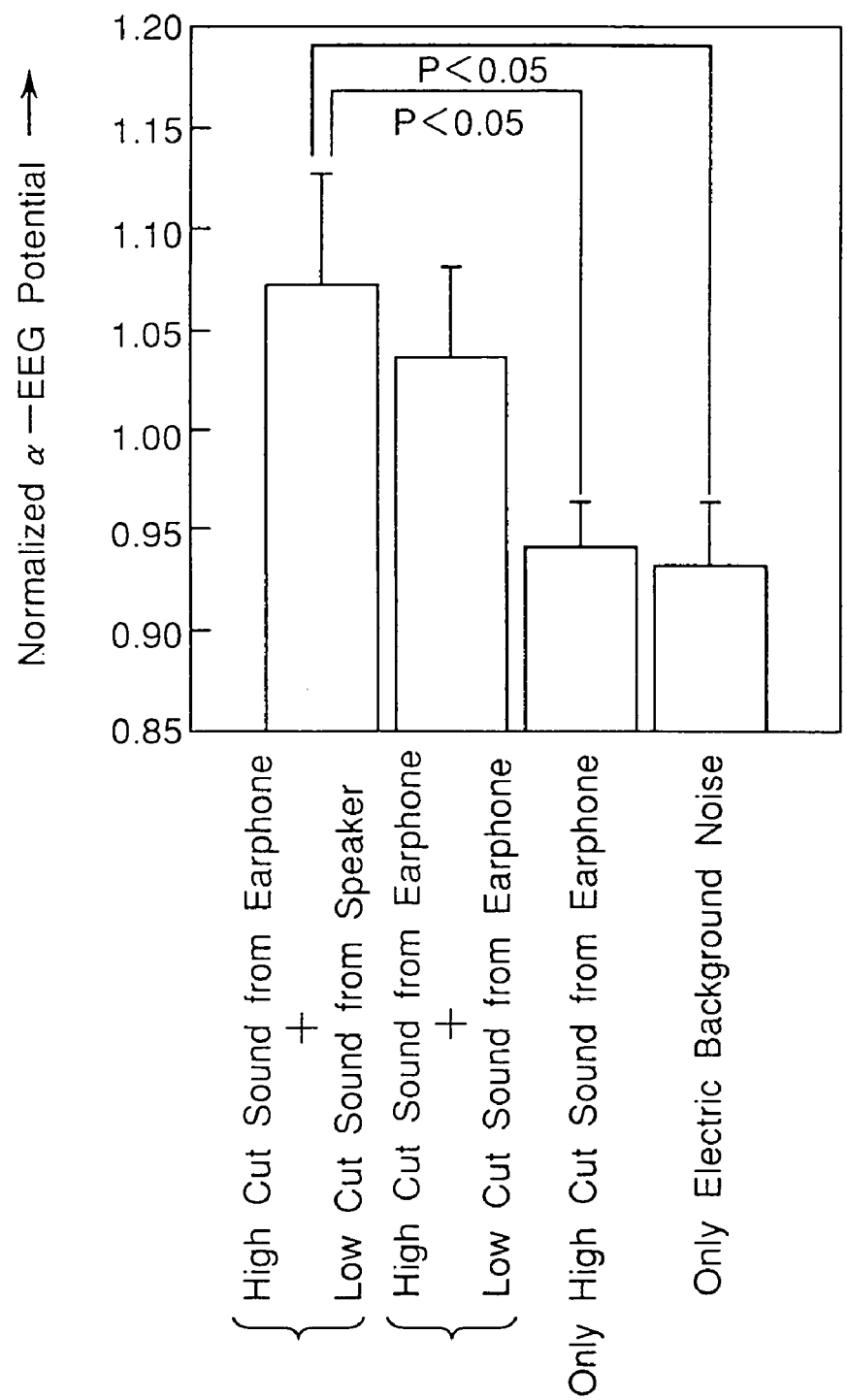
FIG. 18 is a graph showing normalized α-EEG potentials for the respective sounds in the second preferred embodiment.

FIG. 18 is a graph showing normalized α-EEG potentials for the respective sounds in the second preferred embodiment. In the second preferred embodiment, signal sounds are applied to the subject person 30 as follows:

(a) Only high cut sounds or low-frequency components are applied via the high cut sound generators 9cba and 9cbb of the earphones 9ca and 9cb (only the high cut sounds from the earphones 9ca and 9cb);

(b) With the switch SW3 turned to the earphones 9ca and 9cb, low cut sounds or high-frequency components are applied via the low cut sound generators 9caa and 9cab of the earphones 9ca and 9cb, while high cut sounds or low-frequency components are applied via the high cut sound generators 9cba and 9cbb of the earphones 9ca and 9cb ((the low cut sounds from the earphones 9ca and 9cb)+(the high cut sounds from the earphones 9ca and 9cb));

(c) With the switch SW3 turned to the earphones 9ca and 9cb, only electronic background noise is applied via the low cut sound generators 9caa and 9cab and the high cut sound generators 9cba and 9cbb of the earphones 9ca and 9cb (only electronic background noise); and (d) With the switch SW3 turned to the speakers 9aa and 9ab, low cut sounds or high-frequency components are applied via the speakers 9aa and 9ab, while high cut sounds or low-frequency components are applied via the high cut sound generators 9cba and 9cbb of the earphones 9ca and 9cb ((the low cut sounds from the speakers 9aa and 9ab)+(the high cut sounds from the earphones 9ca and 9cb)).

As apparent from FIG. 18, it can be seen that the α-EEG potential increases in the case (d), as compared with those in the cases (a), (b), and (c).

Figure 19A:
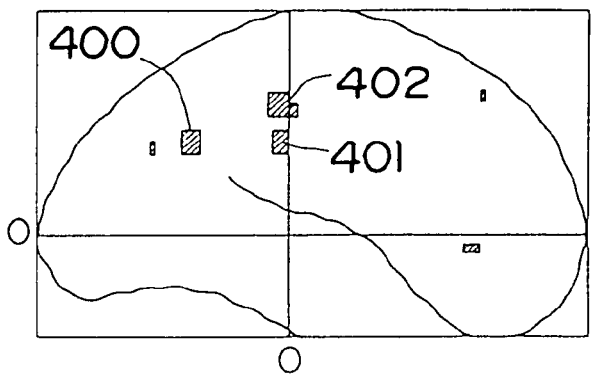
FIGS. 19A, 19B and 19C are projections showing parts in which the r-CBF value more significantly increases when the audible sound is applied from earphones while the low cut sound is applied from speakers, than that when only the audible sound is applied from earphones, in the second preferred embodiment, where
Figure 19B:
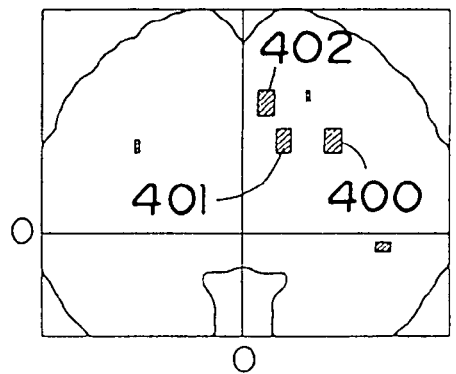
Figure 19C:
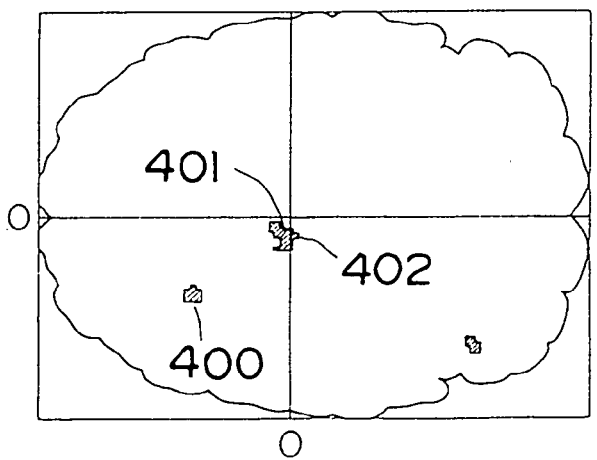

FIGS. 19A, 19B and 19C are projections showing parts or sites 400, 401 and 402 of the brain in which the r-CBF values more significantly increase when the audible sound is applied from the earphones 9ca and 9cb while the low cut sound is applied from the speakers 9aa and 9ab, than that when only the audible sound is applied from the earphones 9ca and 9cb, in the second preferred embodiment, where FIG. 19A is a sagittal projection which is a projection along the sagittal suture of the human skull, FIG. 19B is a coronal projection which is a projection along the coronal suture of the skull, and FIG. 19C is a transversal projection of the skull.

As apparent from FIGS. 19A, 19B and 19C, it can be seen that the cerebral blood flows statistically significantly increase at the three sites including the site 400 belonging to the angular gyrus located at the right brain, the site 401 belonging to the posterior cingulate gyrus, and the position 402 of the boundary of the posterior cingulate gyrus (precuneus).

Figure 20:
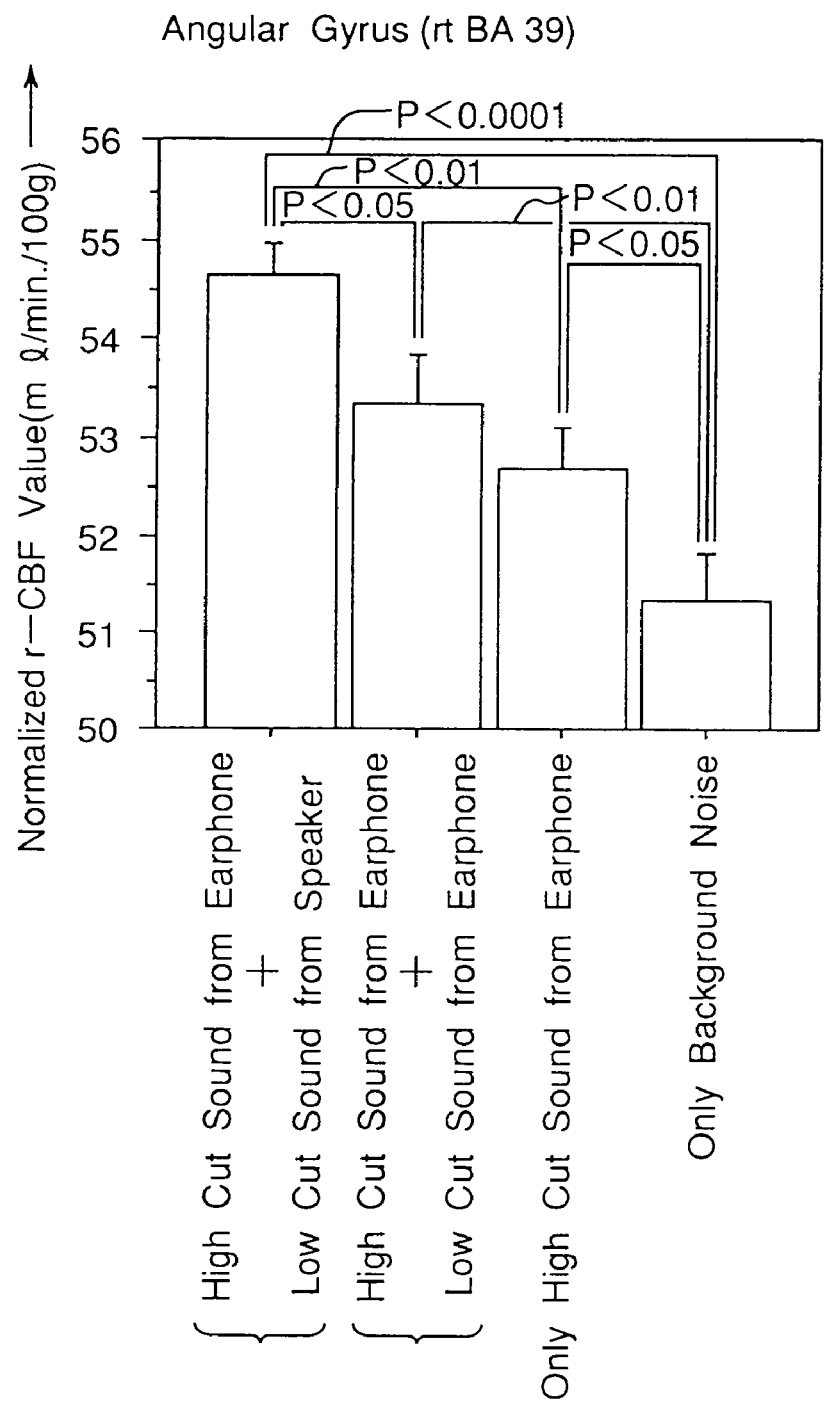
FIG. 20 is a graph showing normalized r-CBF values for the respective sounds at the angular gyrus of the brain in the second preferred embodiment.
Figure 21:
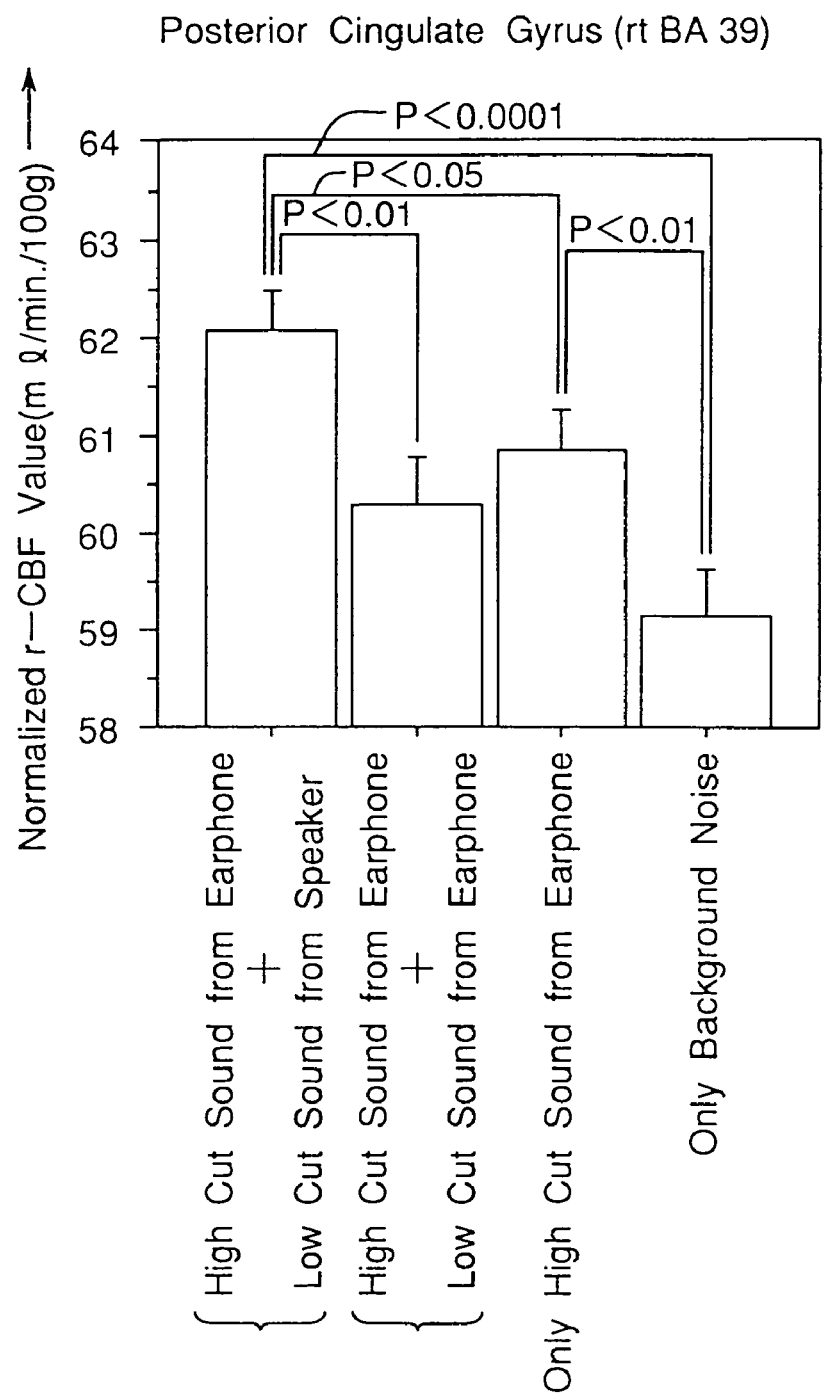
FIG. 21 is a graph showing normalized r-CBF values for the respective sounds at the posterior cingulate gyrus of the brain in the second preferred embodiment.
Figure 22:
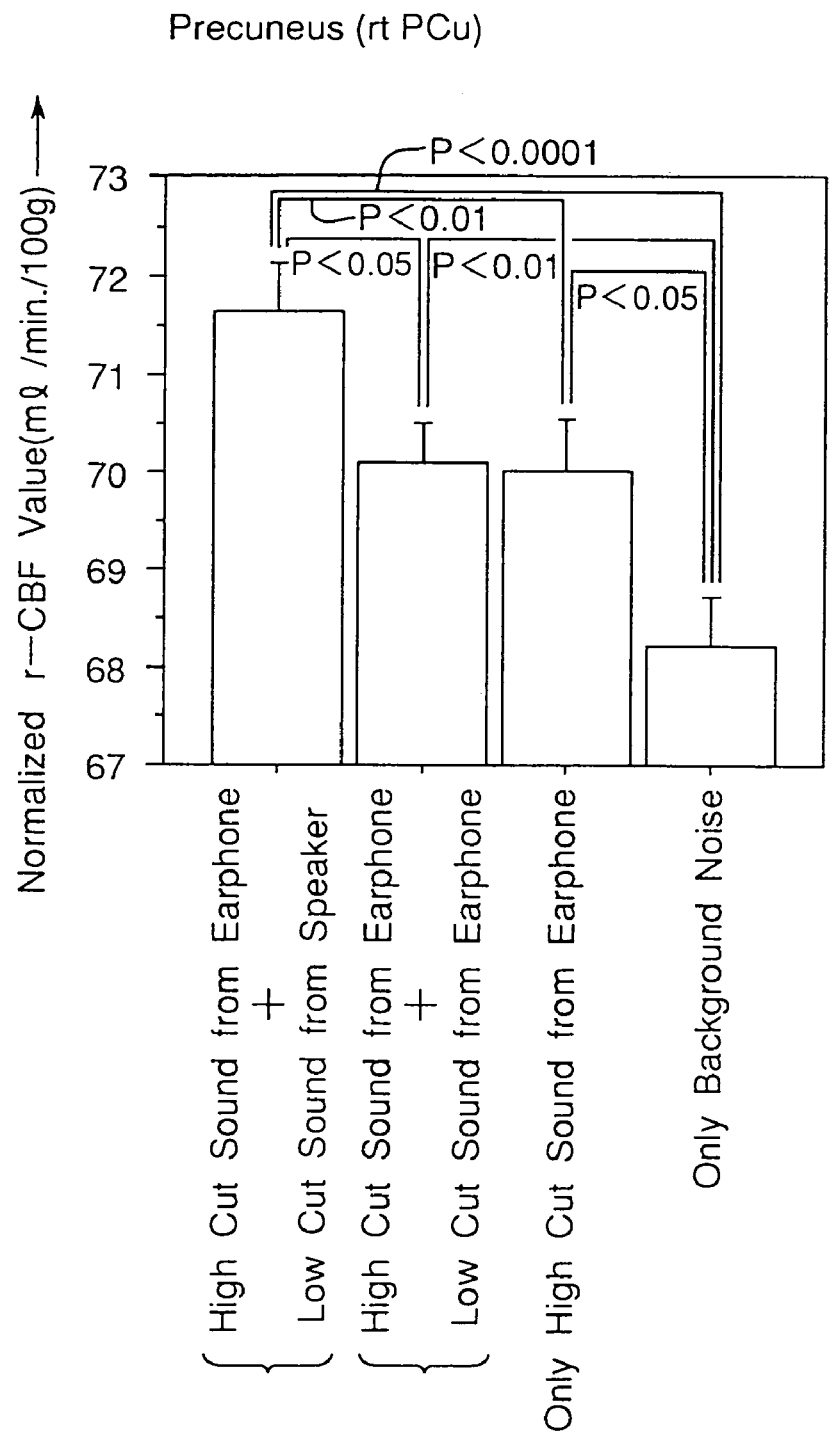
FIG. 22 is a graph showing normalized r-CBF values for the respective sounds at the boundary of the posterior cingulate gyrus (precuneus) of the brain in the second preferred embodiment.

FIG. 20 is a graph showing normalized r-CBF values for the respective sounds at the angular gyrus of the brain in the second preferred embodiment. FIG. 21 is a graph showing normalized r-CBF values for the respective sounds at the posterior cingulate gyrus of the brain in the second preferred embodiment. FIG. 22 is a graph showing normalized r-CBF values for the respective sounds at the boundary of the posterior cingulate gyrus (precuneus) of the brain in the second preferred embodiment.

As apparent from FIGS. 20 to 22, it can be seen that, at the three sites of the brain including the angular gyrus of the brain, the posterior cingulate gyrus thereof, and the boundary of the posterior cingulate gyrus thereof, the cerebral blood flows statistically significantly increase when high cut sounds are applied from the earphones 9ca and 9cb and low cut sounds are applied from the speakers 9aa and 9ab, as compared with that when only background noise is applied, that when only high cut sounds are applied from the earphones 9ca and 9cb, and that when high cut sounds and low cut sounds are applied from the earphones 9ca and 9cb.

Figure 23A:
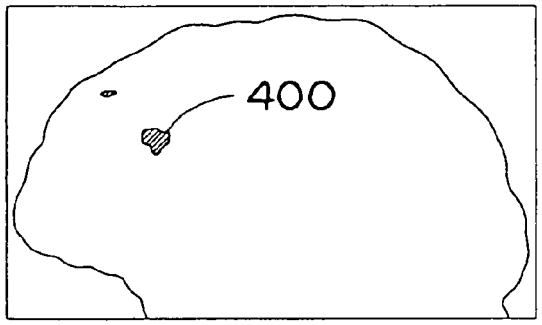
FIGS. 23A, 23B and 23C are sectional views respectively corresponding to FIGS. 19A, 19B and 19C in the second preferred embodiment, and showing a part of the angular gyrus of the brain in which the r-CBF value significantly increases, where
Figure 23B:
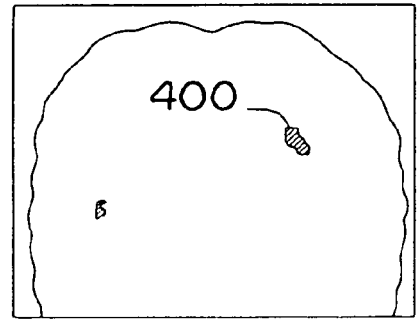
Figure 23C:
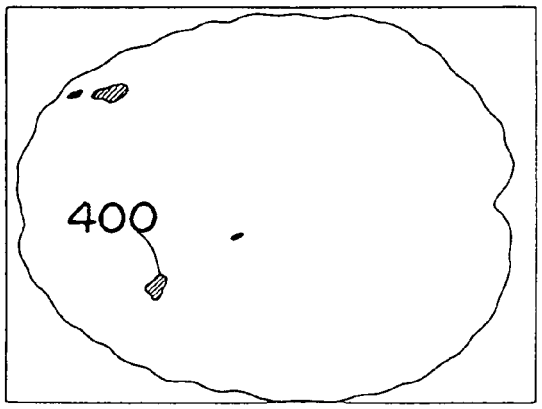
Figure 24A:
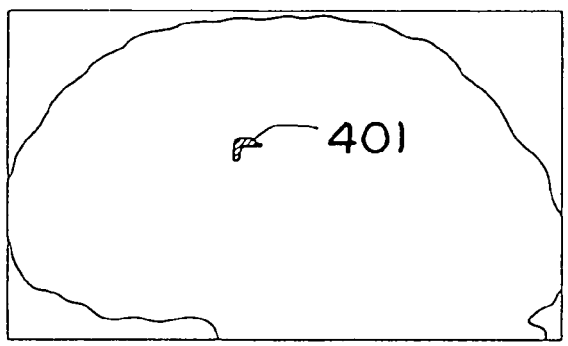
FIGS. 24A, 24B and 24C are sectional views respectively corresponding to FIGS. 19A, 19B and 19C in the second preferred embodiment, and showing a part of the posterior cingulate gyrus of the brain in which the r-CBF value significantly increases, where
Figure 24B:
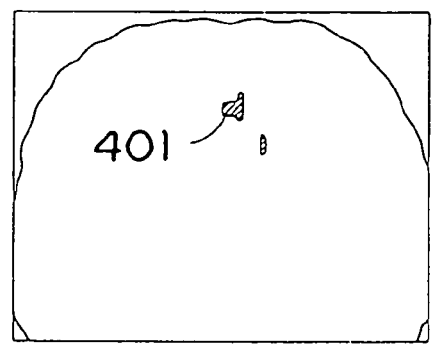
Figure 24C:
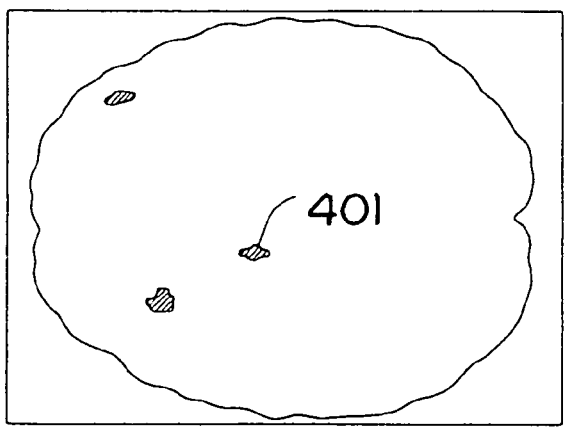
Figure 25A:
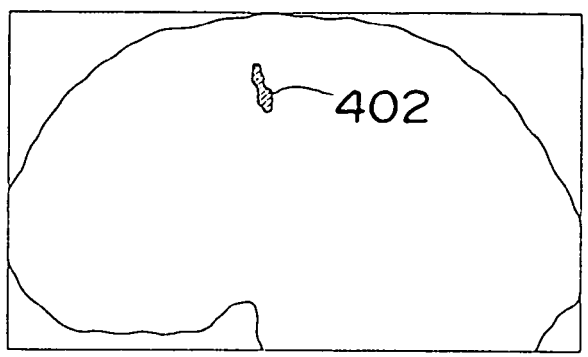
FIGS. 25A, 25B and 25C are sectional views respectively corresponding to FIGS. 19A, 19B and 19C in the second preferred embodiment, and showing a part of the boundary of the posterior cingulate gyrus (precuneus) of the brain in which the r-CBF value significantly increases, where
Figure 25B:
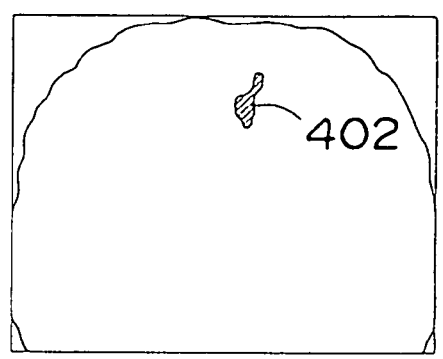
Figure 25C:
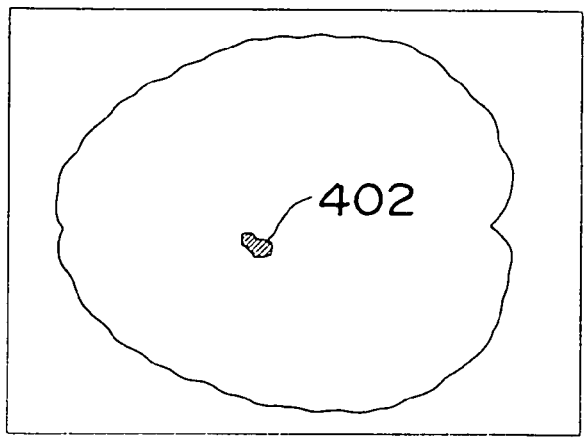

FIGS. 23A, 23B and 23C are sectional views respectively corresponding to FIGS. 19A, 19B and 19C in the second preferred embodiment, and showing a part 400 of the Talairach coordinates (x, y, z)=(28 mm, −54 mm, 28 mm) corresponding to the angular gyrus of the brain in which the r-CBF value significantly increases, where FIG. 23A is a longitudinal sectional view showing a sagittal cross section along the sagittal suture of the human skull, FIG. 23B is a longitudinal sectional view showing a coronal cross section along the coronal suture of the skull, and FIG. 23C is a transversal cross sectional view of the skull. FIGS. 24A, 24B and 24C are sectional views respectively corresponding to FIGS. 19A, 19B and 19C in the second preferred embodiment, and showing a part 401 of the Talairach coordinates (x, y, z)=(14 mm, −34 mm, 32 mm) corresponding to the posterior cingulate gyrus of the brain in which the r-CBF value significantly increases, where FIG. 24A is a longitudinal sectional view showing a sagittal cross section along the sagittal suture of the human skull, FIG. 24B is a longitudinal sectional view showing a coronal cross section along the coronal suture of the skull, and FIG. 24C is a transversal cross sectional view of the skull. Further, FIGS. 25A, 25B and 25C are sectional views respectively corresponding to FIGS. 19A, 19B and 19C in the second preferred embodiment, and showing a part 402 of the Talairach coordinates (x, y, z)=(10 mm, −30 mm, 44 mm) corresponding to the boundary of the posterior cingulate gyrus (precuneus) of the brain in which the r-CBF value significantly increases, where FIG. 25A is a longitudinal sectional view showing a sagittal cross section along the sagittal suture of the human skull, FIG. 25B is a longitudinal sectional view showing a coronal cross section along the coronal suture of the skull, and FIG. 25C is a transversal cross sectional view of the skull.

As shown in FIG. 20 and FIGS. 23A, 23B and 23C, the part of the brain corresponding to the angular gyrus of the right brain which showed the increase in the cerebral blood flows are said to be the site having relations to the perception of space, the perception of sites of the body, and the like. Also, as shown in FIG. 21 and FIGS. 24A, 24B and 24C, the part of the brain belonging to the posterior cingulate gyrus which showed the increase in the cerebral blood flow are said to form a part of the limbic system and to serve for the interface with emotions and actions. Further, as shown in FIG. 22 and FIGS. 25A, 25B and 25C, the part of the brain belonging to the boundary of the posterior cingulate gyrus (precuneus) which showed the increase in the cerebral blood flows are said to be sites containing various kinds of functions including the association function in the cerebrum.

As described above, in the second preferred embodiment, it is apparent that the α-EEG potential increases and moreover the cerebral blood flow increases at the three sites including a site of the angular gyrus of the brain, a site within the posterior cingulate gyrus, and a site of the boundary of the posterior cingulate gyrus, more significantly when high cut sounds are applied via the high cut sound generators 9cba and 9cbb of the earphones 9ca and 9cb while low cut sounds are applied via the speakers 9aa and 9ab ((the high cut sounds from the earphones 9ca and 9cb)+(the low cut sounds from the speakers 9aa and 9ab)). By applying the high cut sounds directly to the auditory sensation and applying the low cut sounds to not only the auditory sensation but also the whole body of the subject person 30, the α-EEG potential can be increased while the cerebral blood flow can be increased, so that the person 30 can be relieved from strains thereby being relaxed, and thus freed from stresses.

Modified Preferred Embodiments

In the above-mentioned preferred embodiments, the Gamelan ensemble 1 is used to generate or to record and reproduce the instrumental sounds of the Gamelan ensemble 1. However, the present invention is not limited to this, and in the present invention, an analog signal synthesizing process or a digital signal synthesizing process used in synthesizers may be used to generate a signal sound which includes the audible frequency range from about 20 Hz up to 20 kHz as well as an extremely high frequency range beyond the audible range and up to 150 kHz, and yet which has fluctuations present in the micro-temporal area within 1 second or 1/10 second in frequency components above 10 kHz, that is, a signal sound in which there exist non-stationary signal sounds changing in the micro-temporal area in the frequency components. Also, the frequency components of the instrumental sounds may have frequencies of the audible frequency range from about 20 Hz to 20 kHz as well as frequencies beyond the audible range and up to 100 kHz.

The above-mentioned preferred embodiments have been described on the signal sound generating apparatuses, each of which records instrumental sounds of the Gamelan ensemble and thereafter reproduces them to generate the instrumental sounds. However, the present invention is not limited to this, and the signal sound generating apparatus may be one which generates sound waves, or sounds, propagated by aerial vibrations that are caused by vibrations of various objects, such as:

(a) sounds produced or generated by musical instruments including percussion instruments, stringed instruments, wind instruments, and keyboard instruments, without being limited to the Gamelan ensemble;

(b) sounds produced or generated by electronic instrumental apparatuses that electronically produce or generate instrumental sounds, including synthesizers;

(c) sounds produced or generated physically or mechanically by vibrating an object;

(d) sounds produced or generated by animals or plants including man or birds and beasts;

(e) sounds produced or generated by natural topographies or other natural environments including, for example, waterfalls and rivers; and (f) sounds electrically produced or generated by signal processing including analog signal processing or digital signal processing.

In the above-mentioned preferred embodiments, the space for generating sounds has been exemplified by the room 20 and 20a. However, the present invention is not limited to this, and the space may be any of the spaces at which sounds will be generated, including indoor spaces, vehicles such as trains, automobiles, airplanes, ships, or the like, or outdoor spaces such as gardens, parks, forests or the like.

In the above-mentioned preferred embodiments, the high cut sounds have been frequency components below 22 kHz. The high cut sounds may also be frequency components of, for example, below 26 kHz to about 20 Hz, or frequency components of below 22 kHz–20 kHz, to about 20 Hz.

As described in detail hereinabove, according to the sound generating apparatus of the preferred embodiments according to the present invention, the sound generating apparatus generates a sound which has a frequency within a first frequency range beyond audible frequency range and up to a predetermined maximum frequency, and which is non-stationary so as to change in a micro-temporal area in a second frequency range beyond 10 kHz, and then the sound is applied to a person, thereby increasing the cerebral blood flows of the person. Therefore, by applying such sounds to the person, the α-EEG potential can be increased so that the person can be relieved from any strains and thereby being relaxed, with stresses dissipated, and that the comfortability of the mind as well as the health of the body can be enhanced or maintained successful.

According to the sound generating apparatus of the preferred embodiments according to the present invention, the sound generating apparatus generates a sound which has a frequency within a first frequency range beyond audible frequency range and up to a predetermined maximum frequency, and which is non-stationary so as to change in a micro-temporal area in a second frequency range beyond 10 kHz, and then, the first sound components within the audible frequency range out of the sound are applied to an auditory sensation of a person and, besides, the second sound components having a frequency range beyond the audible frequency range out of the sound are applied to the person, thereby increasing the cerebral blood flows of the person. Therefore, by applying such sounds to the person, the α-EEG potential can be increased so that the person can be relaxed, with stresses dissipated, and that the comfortability of the mind as well as the health of the body can be enhanced or maintained successful.

According to the sound generating space of the preferred embodiments according to the present invention, the sound generating space comprises an approach for generating a sound which has a frequency within a first frequency range beyond audible frequency range and up to a predetermined maximum frequency, and which is non-stationary so as to change in a micro-temporal area in a second frequency range beyond 10 kHz, wherein the sound is applied to a person, thereby increasing the cerebral blood flows of the person. Therefore, by applying such sounds to the person, the α-EEG potential can be increased so that the person can be relaxed, with stresses dissipated, and that the comfortability of the mind as well as the health of the body can be enhanced or maintained successful.

According to the sound generating space of the preferred embodiments according to the present invention, the sound generating space comprises an approach for generating a sound which has a frequency within a first frequency range beyond audible frequency range and up to a predetermined maximum frequency, and which is non-stationary so as to change in a micro-temporal area in a second frequency range beyond 10 kHz, wherein the first sound components within the audible frequency range out of the sound are applied to an auditory sensation of a person while the second sound components having a frequency range beyond the audible frequency range out of the sound are applied to the person, thereby increasing the cerebral blood flows of the person. Therefore, by applying such sounds to the person as described above, the α-EEG potential can be increased so that the person can be relaxed, with stresses dissipated, and that the comfortability of the mind as well as the health of the body can be enhanced or maintained successful.

According to the sound of the preferred embodiments according to the present invention, the sound is one which has a frequency within a first frequency range beyond audible frequency range and up to a predetermined maximum frequency, and which is non-stationary so as to change in a micro-temporal area in a second frequency range beyond 10 kHz, wherein, when the sound is applied to a person, this causes the cerebral blood flows of the person to be increased. Therefore, by applying the sound to the person as described above, the α-EEG potential can be increased so that the person can be relaxed, with stresses dissipated, and that the comfortability of the mind as well as the health of the body can be enhanced or maintained successful.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A sound generating apparatus comprising:

means for generating a sound including a first frequency range that ranges from above a predetermined audible frequency range to a predetermined maximum frequency, wherein said generated sound is in a non-stationary state so as to change in a micro-temporal area in a second frequency range above 10 kHz; and means for applying said sound to a person, thereby increasing cerebral blood flow of the person as indicated by increased α-EEG activity of the person's brain, wherein said means for generating includes a switch for cutting off the audible frequency range of said sound from being applied to the person and wherein the non-stationary state characteristic of the generated sound is required for generating a hyper sonic effect to increase α-EEG activity of the person's brain in an effort to reduce human stress.

2. The sound generating apparatus as claimed in claim 1, wherein the maximum frequency is 150 kHz.

3. The sound generating apparatus of claim 1, wherein said sound includes a high-frequency component ranging from 20–150 kHz,
wherein said high frequency component is temporarily in a non-stationary state above 10 kHz.

4. The sound generating apparatus as claimed in claim 1 further comprising:
means for analyzing the sound by using a Maximum Entropy Method (MEM) in order to obtain a MEM spectra; and
means for displaying the MEM spectra.

5. A sound generating space comprising:
means for generating a sound including a first frequency range that ranges from above a predetermined audible frequency range to a predetermined maximum frequency, wherein said generated sound is in a non-stationary state so as to change in a micro-temporal area in a second frequency range above 10 kHz; and
means for applying said sound to a person, thereby increasing cerebral blood flow of the person as indicated by increased α-EEG activity of the person's brain, wherein said means for generating includes a switch for cutting off the audible frequency range of said sound from being applied to the person and wherein the non-stationary state characteristic of the generated sound is required for generating a hyper sonic effect to increase α-EEG activity of the person's brain in an effort to reduce human stress.

6. The sound generating apparatus as claimed in claim 5, wherein the maximum frequency is 150 kHz.

7. The sound generating apparatus of claim 5, wherein said sound includes a high-frequency component ranging from 20–150 kHz,
wherein said high frequency component is temporarily in a non-stationary state above 10 kHz.

8. A sound which is generated by a sound generating apparatus composed of a switch for cutting off a frequency range in the audible frequency range, said generated sound being in a non-stationary state so as to change in a micro-temporal area in a second frequency range above 10 kHz, and which has a frequency ranging from above a predetermined audible frequency range to a predetermined maximum frequency, said generated sound being applied to a person, thereby increasing cerebral blood flow of the person, wherein said switch cuts off the audible frequency range of said sound from being applied to the person.

9. The sound generating apparatus as claimed in claim 8, wherein the maximum frequency of the generated sound is 150 kHz.

10. The sound generating apparatus of claim 8, wherein said generated sound includes a high-frequency component ranging from 20–150 kHz, wherein said high frequency component is temporarily in a non-stationary state above 10 kHz.

11. A method for generating a sound, comprising:
switching on a first switch and a second switch, said first switch for cutting off sound in a first frequency range and said second switch for cutting off sound in a second frequency range different from the first frequency range;
generating a sound in said first frequency range that ranges from above a predetermined audible frequency range to a predetermined maximum frequency, wherein said generated sound is in a non-stationary state so as to change in a micro-temporal area in a frequency range above 10 kHz; and
applying said sound to a person, thereby increasing cerebral blood flow of the person as indicated by increased α-EEG activity of the person's brain, wherein said second switch cuts off the second frequency range from being applied to the person and wherein the non-stationary state characteristic of the generated sound is required for generating a hyper sonic effect to increase α-EEG activity of the person's brain in an effort to reduce human stress.

12. The sound generating apparatus of claim 11, wherein said generated sound includes a high-frequency component ranging from 20–150 kHz,
wherein said high frequency component is temporarily in a non-stationary state above 10 kHz.

13. A sound generating apparatus comprising:
means for generating a sound in a first frequency range within the audible frequency range and a second frequency range that ranges from above a predetermined audible frequency range to a predetermined maximum frequency, wherein said generated sound in the second frequency range is in a non-stationary state so as to change in a micro-temporal area in a second frequency range above 10 kHz;
means for applying first sound components of said sound in the first frequency range directly to an auditory sensation of a person, said means for applying first sound components comprising a pair of earphones; and
a loudspeaker applying second sound components that are above the audible frequency range substantially throughout the entire body of said person, for increasing cerebral blood flow of the person as indicated by increased α-EEG activity of the person's brain, wherein the non-stationary state characteristic of the generated sound is required for generating a hyper sonic effect to increase α-EEG activity of the person's brain in an effort to reduce human stress.

14. The sound generating apparatus as claimed in claim 13, wherein the maximum frequency is 150 kHz.

15. The sound generating apparatus of claim 13, wherein said second sound component includes a high-frequency component ranging from 20–150 kHz,
wherein said high frequency component is temporarily in a non-stationary state above 10 kHz.

16. A sound generating space comprising:
means for generating a sound in a first frequency range within the audible frequency range and a second frequency range that ranges from above a predetermined audible frequency range to a predetermined maximum frequency, wherein said generated sound in said second frequency range is in a non-stationary state so as to change in a micro-temporal area in a second frequency range above 10 kHz;
means for applying first sound components of said sound in the first frequency range directly to an auditory sensation of a person, said means for applying first sound components including a pair of earphones; and
loudspeaker applying second sound components that are above the audible frequency range substantially throughout the entire body of said person, for increasing cerebral blood flow of the person as indicated by increased α-EEG activity of the person's brain, wherein the non-stationary state characteristic of the generated sound is required for generating a hyper sonic effect to increase α-EEG activity of the person's brain in an effort to reduce human stress.

17. The sound generating apparatus as claimed in claim 16, wherein the maximum frequency is 150 kHz.

18. The sound generating apparatus of claim 16, wherein said second sound component includes a high-frequency component ranging from 20–150 kHz, wherein said high frequency component is temporarily in a non-stationary state above 10 kHz.

19. A method for generating a sound, comprising:

generating a sound in a first frequency range within the audible frequency range and a second frequency range that ranges from above a predetermined audible frequency range to a predetermined maximum frequency, wherein said generated sound in said second frequency range is in a non-stationary state so as to change in a micro-temporal area in a second frequency range above 10 kHz;

applying first sound components of said sound in the first frequency range directly to an auditory sensation of a person through a pair of earphones; and applying second sound components that are above the audible frequency range substantially throughout the entire body of said person through a loudspeaker, for increasing cerebral blood flow of the person as indicated by increased α-EEG activity of the person's brain, wherein the non-stationary state characteristic of the generated sound is required for generating a hyper sonic effect to increase α-EEG activity of the person's brain in an effort to reduce human stress.

20. The sound generating apparatus of claim 19, wherein said sound includes a high-frequency component ranging from 20–150 kHz, wherein said high frequency component is temporarily in a non-stationary state above 10 kHz.

* * * * *

UNITED STATES PATENT AND TRADEMARK OFFICE
CERTIFICATE OF CORRECTION

| | |
|---|---|
| PATENT NO. | : 7,079,659 B1 |
| APPLICATION NO. | : 08/723955 |
| DATED | : July 18, 2006 |
| INVENTOR(S) | : Tsutomu Oohashi et al. |

It is certified that error appears in the above-identified patent and that said Letters Patent is hereby corrected as shown below:

On the Title Page:

[75] change the fourth inventor's name from "Fuwamotot" to --Fuwamoto--.

Signed and Sealed this

Twenty-sixth Day of December, 2006

JON W. DUDAS
*Director of the United States Patent and Trademark Office*